US010023697B2

(12) United States Patent
Breyta et al.

(10) Patent No.: US 10,023,697 B2
(45) Date of Patent: Jul. 17, 2018

(54) CONDENSATION POLYMERS FOR ANTIMICROBIAL APPLICATIONS

(71) Applicants: International Business Machines Corporation, Armonk, NY (US); AGENCY FOR SCIENCE, TECHNOLOGY AND RESEARCH, Singapore (SG)

(72) Inventors: Gregory Breyta, San Jose, CA (US); Julian M. W. Chan, Fremont, CA (US); Daniel J. Coady, Bluffton, GA (US); Amanda C. Engler, Woodbury, MN (US); Jeannette M. Garcia, San Jose, CA (US); Wei Han, San Jose, CA (US); James L. Hedrick, Pleasanton, CA (US); Alshakim Nelson, Montlake, WA (US); Robert J. Ono, San Jose, CA (US); Yi Yan Yang, Singapore (SG); Mu San Zhang, San Jose, CA (US)

(73) Assignees: International Business Machines Corporation, Armonk, NY (US); Agency For Science, Technology And Research, Singapore (SG)

(*) Notice: Subject to any disclaimer, the term of this patent is extended or adjusted under 35 U.S.C. 154(b) by 0 days.

(21) Appl. No.: 15/361,313

(22) Filed: Nov. 25, 2016

(65) Prior Publication Data
US 2017/0073471 A1    Mar. 16, 2017

Related U.S. Application Data

(62) Division of application No. 14/705,451, filed on May 6, 2015, now Pat. No. 9,580,554.

(51) Int. Cl.
| | |
|---|---|
| C08G 73/06 | (2006.01) |
| C08G 69/48 | (2006.01) |
| C08G 73/02 | (2006.01) |
| A01N 43/60 | (2006.01) |
| A01N 37/44 | (2006.01) |
| A61K 8/88 | (2006.01) |
| A61K 31/785 | (2006.01) |
| A61K 31/787 | (2006.01) |
| A61Q 5/02 | (2006.01) |
| A61Q 11/00 | (2006.01) |
| A61Q 15/00 | (2006.01) |
| C11D 3/48 | (2006.01) |
| D21H 17/55 | (2006.01) |

(Continued)

(52) U.S. Cl.
CPC ............ *C08G 69/48* (2013.01); *A01N 37/12* (2013.01); *A01N 37/18* (2013.01); *A01N 37/20* (2013.01); *A01N 37/44* (2013.01); *A01N 43/40* (2013.01); *A01N 43/58* (2013.01); *A01N 43/60* (2013.01); *A01N 47/06* (2013.01); *A61K 8/84* (2013.01); *A61K 8/85* (2013.01); *A61K 8/86* (2013.01); *A61K 8/88* (2013.01); *A61K 31/785* (2013.01); *A61K 31/787* (2013.01); *A61K 45/06* (2013.01); *A61Q 5/02* (2013.01); *A61Q 11/00* (2013.01); *A61Q 15/00* (2013.01); *A61Q 17/00* (2013.01); *A61Q 17/005* (2013.01); *A61Q 19/007* (2013.01); *C08G 63/916* (2013.01); *C08G 64/42* (2013.01); *C08G 73/024* (2013.01); *C08G 73/0206* (2013.01); *C08G 73/028* (2013.01); *C08G 73/0273* (2013.01); *C08G 73/0293* (2013.01); *C08G 73/0633* (2013.01); *C11D 3/3723* (2013.01); *C11D 3/48* (2013.01); *D21H 17/55* (2013.01); *D21H 17/56* (2013.01); *D21H 21/36* (2013.01); *A61K 2800/10* (2013.01); *A61K 2800/74* (2013.01); *C08G 2650/02* (2013.01); *C08G 2650/38* (2013.01); *C08G 2650/58* (2013.01); *C08L 77/04* (2013.01); *C08L 79/02* (2013.01)

(58) Field of Classification Search
CPC ................ A61K 31/785; A61K 31/787; C08G 2650/58; C08G 73/0206
See application file for complete search history.

(56) References Cited

U.S. PATENT DOCUMENTS

| | | |
|---|---|---|
| 3,124,607 A | 3/1964 | Schisla |
| 3,329,657 A | 7/1967 | Strazdins et al. |

(Continued)

FOREIGN PATENT DOCUMENTS

| | | |
|---|---|---|
| EP | 0086066 A1 | 1/1983 |
| JP | 2000265085 A | 9/2000 |

(Continued)

OTHER PUBLICATIONS

PCT International Search Report, WO2016178634, dated Sep. 6, 2016, international application No. PCT/SG2016/050211.

(Continued)

*Primary Examiner* — Gregory Listvoyb
(74) *Attorney, Agent, or Firm* — Michael R. Roberts

(57) ABSTRACT

A number of cationic antimicrobial polymers have been synthesized by a condensation polymerization in bulk. The initial polymer formed has backbone tertiary nitrogens, which are subsequently quaternized using a suitable quaternizing agent (e.g., alkyl halide). The cationic polymers include polyamides, polycarbonates, polypolyureas and polyguanidiniums having a cationic repeat unit comprising the quaternary ammonium nitrogen as a backbone nitrogen. The cationic polymers can be active against Gram-negative, Gram-positive microbes, and/or fungi.

29 Claims, 10 Drawing Sheets

(51) Int. Cl.

| | | |
|---|---|---|
| A61Q 17/00 | (2006.01) | |
| C11D 3/37 | (2006.01) | |
| A01N 43/40 | (2006.01) | |
| A01N 37/18 | (2006.01) | |
| A61K 8/86 | (2006.01) | |
| A61Q 19/00 | (2006.01) | |
| A01N 37/12 | (2006.01) | |
| A01N 37/20 | (2006.01) | |
| A01N 43/58 | (2006.01) | |
| A01N 47/06 | (2006.01) | |
| A61K 8/84 | (2006.01) | |
| A61K 8/85 | (2006.01) | |
| C08G 63/91 | (2006.01) | |
| C08G 64/42 | (2006.01) | |
| A61K 45/06 | (2006.01) | |
| D21H 17/56 | (2006.01) | |
| D21H 21/36 | (2006.01) | |
| C08L 79/02 | (2006.01) | |
| C08L 77/04 | (2006.01) | |

(56) References Cited

U.S. PATENT DOCUMENTS

| | | |
|---|---|---|
| 4,201,766 A | 5/1980 | Grollier et al. |
| 4,315,087 A | 2/1982 | Redmore et al. |
| 4,528,316 A | 7/1985 | Soerens |
| 5,118,785 A | 6/1992 | Speranza et al. |
| 6,548,590 B1 | 4/2003 | Kiloski et al. |
| 7,883,767 B2 | 2/2011 | Childs et al. |
| 8,771,578 B2 | 7/2014 | Campbell |
| 2003/0103929 A1* | 6/2003 | Maubru ............... A61K 8/8152 424/70.16 |
| 2013/0183262 A1 | 7/2013 | Wynne et al. |

FOREIGN PATENT DOCUMENTS

| | | |
|---|---|---|
| JP | 2001071411 A | 3/2001 |
| WO | 2014168762 A1 | 10/2014 |
| WO | 2014168771 A1 | 10/2014 |

OTHER PUBLICATIONS

PCT International Written Opinion, WO2016178634, dated Sep. 6, 2016, international application No. PCT/SG2016/050211.

Tsai, et al., "A New Cationic Poly(ester anhydride): Synthesis, Structure Characterization, and Biological Properties", Polymer Science B, 2012, vol. 54, pp. 420-426.

Zhang, et al., "Step-growth polymerization of highly efficacious antimicrobial polymers for consumer care products", Abstracts of Papers, 251st ACS National Meeting & Exposition, San Diego, CA; United States, Mar. 13-17, 2016, published Feb. 25, 2016.

Katsarava, et al., "Synthesis of Polyurethanes by Polycondensation of Activated Diol Biscarbonates with Diamines in Mild Conditions", Polymer Science USSR, 1987, vol. 29, p. 2268-2275.

Lee, et al., "Quaternized Polyamidoamine Dendrimers as Novel Gene Delivery System: Relationship between Degree of Quaternization and Their Influences," Bull. Korean Chem. Soc., 2003, vol. 24, 1637-1640.

Monsalve, et al., "Lipase-catalyzed synthesis and characterization of a novel linear polyamidoamine oligomer", Polymer, vol. 51, Issue 14, Jun. 24, 2010, pp. 2998-3005.

* cited by examiner

CONDENSATION POLYMERS FOR ANTIMICROBIAL APPLICATIONS

This invention was made under a joint research agreement between International Business Machines Corporation and the Agency For Science, Technology and Research.

BACKGROUND

The present invention relates to condensation polymers for antimicrobial applications, and more specifically, to cationic forms of polycondensation polymers for topical antibacterial use.

Antimicrobial agents are commonly used in personal care products to inhibit microbial growth and infections therefrom, and product decomposition. Most antimicrobial agents used in these products are small molecules, including anilides (e.g., triclocarban), bis-phenols (e.g., triclosan), biguanides (e.g., chlorhexidine) and quaternary ammonium compounds (e.g., cetylpyridium chloride and cetrimide). Among them, triclosan is one of the most extensively used compounds. Triclosan is present in more than 50% of consumer products including soap, deodorant, toothpaste, mouth wash, cosmetics (e.g., Garden Botanika® Powder Foundation, Mavala Lip Base, Jason Natural Cosmetics and Movate® Skin Litening Cream HQ), cleaning supplies, kitchen utensils, children's toys, bedding, socks, shoes and trash bags. It is effective against Gram-positive bacteria, while it has little activity against *P. aeruginosa* (Gram-negative bacteria) and molds. At high concentrations, it is biocidal with multiple cytoplasmic and membrane targets. However, at low concentrations, it is bacteriostatic by inhibiting fatty acid synthesis. On the other hand, triclosan has cumulative and persistent effects on the skin. It was found in human breast milk and urine samples. At minimal concentrations of triclosan ($<$g/L) and chlorine ($<$mg/L), common household tap water levels, triclosan can degrade to form toxic derivatives, 2,4-dichlorophenol and 2,4,6-trichlorophenol. Moreover, in sunlight and wastewater chlorine treatment, it also forms highly toxic carcinogenic dioxin-like compounds. After use, it is discharged into water. Triclosan was found in 85 out of 139 streams and rivers in 30 states in the US, and is toxic to aquatic species. It is persistent in the environment, and was detected in sediments in a Swiss lake as far back as the 1960s. Therefore, the use of triclosan in consumer products will be banned in Europe and in the United States within 2 years.

Many strains of bacteria spores (e.g., *Clostridium* species), Gram-positive bacteria (e.g., mycobacteria) and Gram-negative bacteria (e.g., *Pseudomonas aeruginosa* (*P. aeruginosa*)) have intrinsic resistance to the antimicrobial agents listed above. Moreover, these antimicrobial agents are not effective against biofilms. For example, *Serratia marcescens* (*S. marcescens*) and *Burkholderia cepacia* (*B. cepacia*) biofilms were found in disinfectant chlorhexidine solution, *P. aeruginosa* biofilm in iodophor antiseptics and on the interior surface of polyvinyl chloride pipes used in the production of providone-iodine antiseptics. Overuse of these antimicrobial agents has led to drug resistance in microbes. Major concerns include cross-resistance and co-resistance with clinically used antimicrobial agents, which may present a potential public health risk.

Most small molecule antimicrobial agents do not physically damage the cell wall, but rather penetrate the cell wall and act on specific intracellular targets. Consequently, bacterial morphology is preserved, allowing bacteria to easily develop resistance. Antimicrobial peptides (AMPs) have been explored as an alternative. AMPs (e.g., magainins, alamethicin, protegrins and defensins) do not have a specific target in microbes. They interact with microbial membranes based on electrostatic interaction, inducing damage to the microbial membranes by forming pores in the membranes. The physical nature of this action prevents microbes from developing resistance to AMPs. Although efforts have been made to design synthetic peptides with various structures over the last two decades, high manufacturing cost has limited their application in personal care products.

A number of cationic polymers that mimic the facially amphiphilic structure and antimicrobial functionalities of peptides have been proposed that can be more easily prepared at low cost and on large scale compared to peptides. For example, antimicrobial polynorbornene and polyacrylate derivatives, and pyridinium copolymers were synthesized either from amphiphilic monomers (homopolymers) or from cationic (hydrophilic) monomer and hydrophobic comonomer (random copolymers). However, most antimicrobial polymers reported in the literature are non-biodegradable and/or require several steps of synthesis. With the high volume of poorly degradable single-use consumer products already destined for landfills, the problem would be exacerbated by the addition of non-biodegradable antimicrobial materials that destroy bacteria and fungi responsible for slow landfill degradation.

A number of biodegradable cationic polycarbonates having high potency towards pathogenic microbes and low toxicity. These cationic polycarbonates degrade in aqueous solution especially in an alkaline environment which is often found in consumer care products. On the other hand, the synthesis of polycarbonates requires several steps like monomer synthesis, ring-opening polymerization and post-quaternization, which can translate into high consumer prices.

Currently, biodegradable, safe and cost-effective antimicrobial agents are needed for use in personal care products that can kill multidrug-resistant bacteria and fungi, remove biofilms, and prevent drug resistance.

SUMMARY

Accordingly, a cationic polymer is disclosed, comprising: a cationic repeat unit of formula (1):

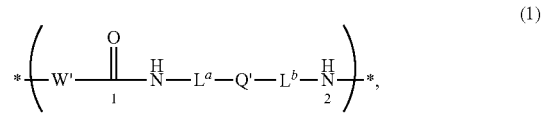

wherein
W' is a single bond or a divalent linking group having a structure *—C(=O)-L'-*, wherein L' is divalent radical comprising 1-20 carbons and L' is linked to carbon 1,
L' is a divalent radical comprising 1-20 carbons,
$L^a$ and $L^b$ are independent divalent hydrocarbon groups comprising 2-20 carbons, and
Q' is a divalent radical comprising a positive-charged nitrogen which is covalently bonded to 4 carbons, and
adjacent repeat units of the cationic polymer are covalently linked in a head-to-tail arrangement, wherein nitrogen labeled 2 is designated a tail and W' is designated a head.

Also disclosed is a method of killing a microbe, comprising contacting the microbe with an above-described cationic polymer.

Also disclosed is an antimicrobial composition comprising an above-described cationic polymer and at least one other chemical component.

The above-described and other features and advantages of the present invention will be appreciated and understood by those skilled in the art from the following detailed description, drawings, and appended claims.

BRIEF DESCRIPTION OF THE SEVERAL VIEWS OF THE DRAWINGS

FIG. 1 is a $^1$H NMR spectrum of cationic polymer P48a.
FIG. 3 is a $^1$H NMR spectrum of cationic polymer P49a.

DETAILED DESCRIPTION

Figure 1:
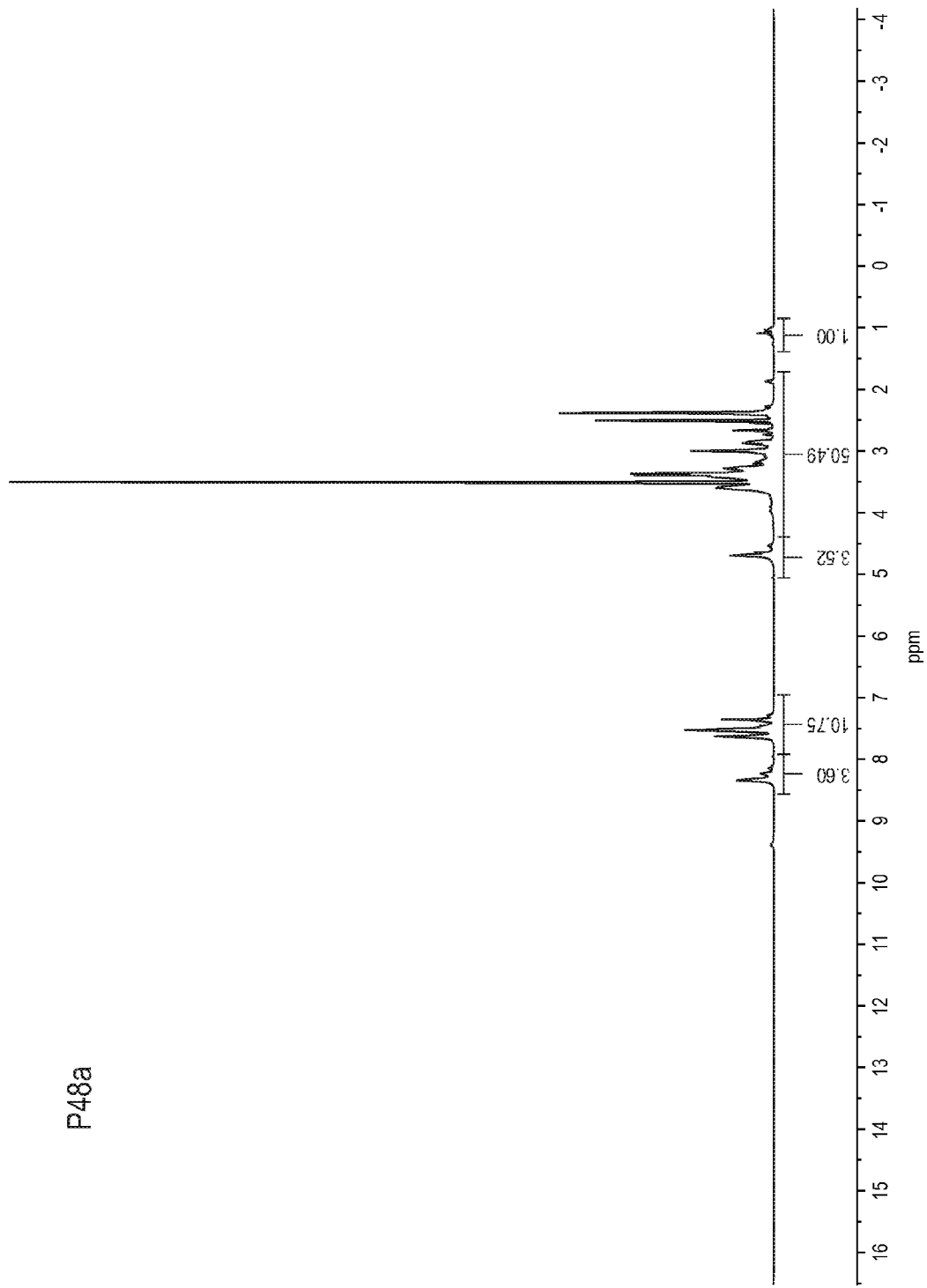

The disclosed cationic polymers are biodegradable materials comprising cationic repeat units having at least one quaternary nitrogen in the polyamine backbone. For this reason, the cationic polymers are also referred to herein as "polyamines". The quaternary nitrogen is a positive-charged nitrogen covalently bonded only to carbons (3 or 4 carbons), and is ionically associated with a negative-charged counterion X$^-$. Preferably, X$^-$ is a free ion, which is not directly or indirectly covalently linked to the polyamine backbone. The polyamines comprise cationic repeat units having a backbone portion that preferably comprise amide, carbamate, and/or urea functional groups. The polyamines are water soluble and can be highly active against Gram-positive microbes (e.g., S. aureus), Gram-negative microbes (e.g., Escherichia coli (E. coli), P. aeruginosa), and fungi (e.g., C. albicans). The polyamines can be biocompatible, biodegradable, non-hemolytic, and non-cytotoxic at concentrations above the minimum inhibitory concentration (MIC), and are therefore attractive for a wide range of consumer products such as, for example, cosmetics, skin lotions, and antibiotic drugs. The polyamines are capable of forming ionic complexes with anionic materials, making them potentially useful as carriers for gene and/or drug delivery applications.

The term "biodegradable" is defined by the American Society for Testing and Materials as degradation caused by biological activity, especially by enzymatic action, leading to a significant change in the chemical structure of the material. For purposes herein, a material is "biodegradable" if it undergoes 60% biodegradation within 180 days in accordance with ASTM D6400. Herein, a material is "enzymatically biodegradable" if the material can be degraded (e.g., depolymerized) by a reaction catalyzed by an enzyme.

A "biocompatible" material is defined herein as a material capable of performing with an appropriate host response in a specific application.

The polyamines are preferably linear homopolymers or linear random copolymers. Herein, a linear polymer has one polymer branch, and the branch has two peripheral ends (i.e., two dangling ends, as in a segment of a rope).

The cationic repeat units have a structure according to formula (1):

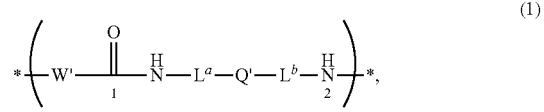

(1)

wherein
W' is a single bond or a divalent linking group having a structure *—C(=O)-L'-*, wherein L' is divalent radical comprising 1-20 carbons and L' is linked to carbon 1,
L$^a$ and L$^b$ are independent divalent hydrocarbon groups comprising 2-20 carbons, and
Q' is a divalent radical comprising a positive-charged nitrogen which is covalently bonded to 4 carbons.

Starred bonds (i.e., bond with an asterisk) represent attachment points for a covalent bond, not methyl groups. An atomic center or group having a starred bond (i.e., shown linked to an asterisk) means the atomic center or group is covalently bonded to another portion of the chemical structure.

When W' is a single bond, the cationic repeat unit has a formula (1A):

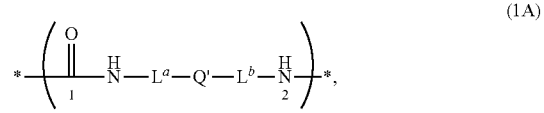

(1A)

and the polyamine backbone comprises a urea group. When W' is *—C(=O)-L'-*, the polyamine backbone can comprise amide, carbamate, and/or urea groups.

The repeat units of the polyamines are linked in a head-to-tail arrangement. The nitrogen end is the tail (e.g., nitrogen labeled 2 of formula (1) is designated the tail), and the opposing end the head. The head of a given repeat unit can be linked to the tail of a different repeat unit or to a polymer chain end group. Likewise, the tail of a given repeat unit can be linked to head of a different repeat unit or to a polymer chain end group.

When present, L' can have any suitable structure. For example, L' can be a divalent hydrocarbon group. Exemplary non-limiting divalent hydrocarbon groups include methylene, 1,1-ethylene, 1,2-ethylene, 1,1-propylene, 1,2-propylene, 1,3-propylene, 1,1-butylene, 1,2-butylene, 1,3-butylene, 1,4-butylene, 1,1-pentylene, 1,2-pentylene, 1,3-pentylene, 1,4-pentylene, 1,5-pentylene, 1,2-cyclohexylene, 1,3-cyclohexylene, 1,4-cyclohexylene, 1,2-phenylene, 1,3-phenylene, and 1,4-phenylene. Accordingly W' can have a structure that includes those of Scheme 1, wherein carbon 1 is linked to carbonyl carbon 1 of formula (1).

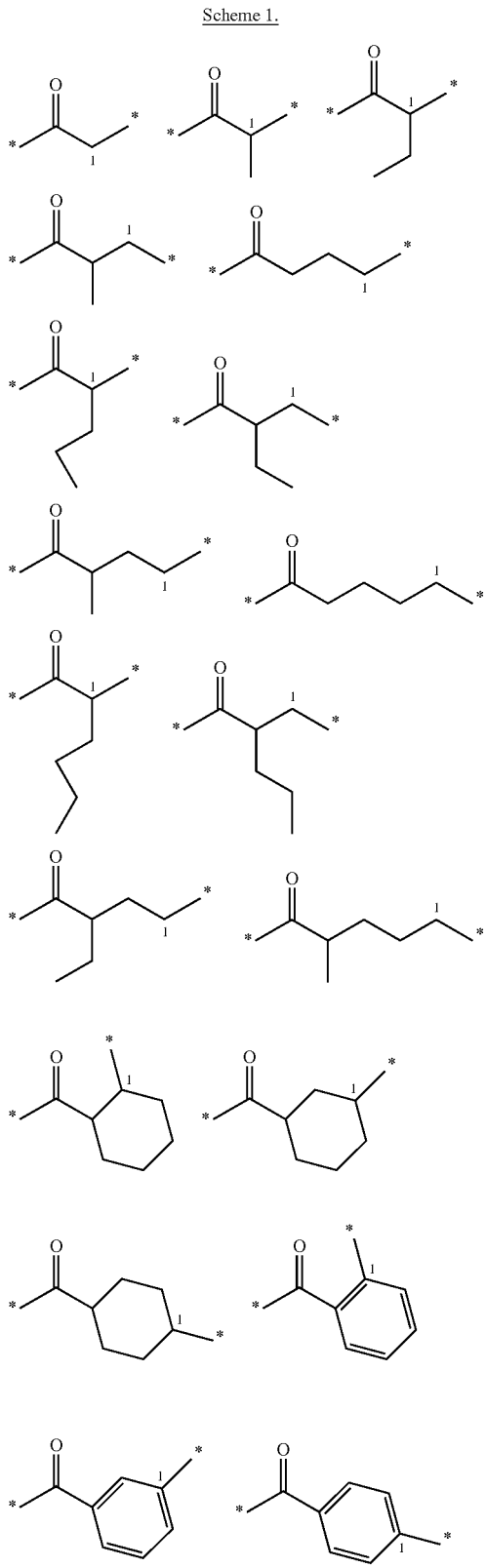

Scheme 1.

Other L' groups include those of Scheme 2.

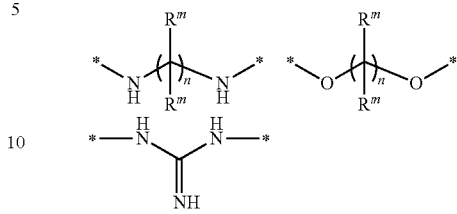

Scheme 2.

wherein n is an integer having a value of 1 to 20, and each $R^m$ is an independent hydrocarbon radical comprising 1-10 carbons. Accordingly, W' can be a divalent radical that includes those of Scheme 3.

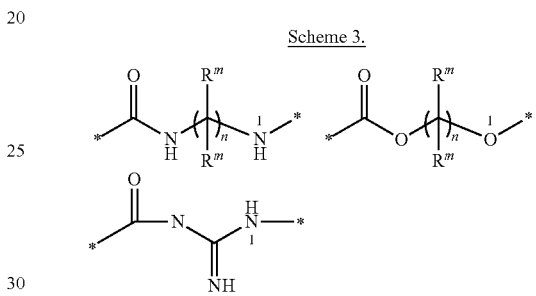

Scheme 3.

In Scheme 3, each n is an independent integer having a value of 1 to 20, each $R^m$ is an independent hydrocarbon radical comprising 1-10 carbons, and the nitrogen or oxygen labeled 1 is linked to carbonyl carbon 1 of formula (1).

In an embodiment, L' is

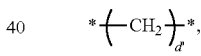

wherein d' is an integer having a value of 1 to 6. In this instance, W' is

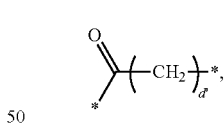

wherein d' is an integer having a value of 1 to 6, and the starred bond of the methylene carbon is linked to the carbon 1 of formula (1).

In another embodiment, L' is 1,2-ethylene and W' is

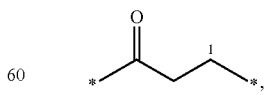

wherein methylene carbon 1 is linked to carbonyl carbon 1 of formula (1).

$L^a$ and $L^b$ can be the same or different hydrocarbon groups. Exemplary non-limiting $L^a$ and $L^b$ groups include 1,1-ethylene, 1,2-ethylene, 1,1-propylene, 1,3-propylene, 1,1-butylene, 1,4-butylene, and 1,1-pentylene, 1,5-pentylene, 1,2-cyclohexylene, 1,3-cyclohexylene, 1,4-cyclohexylene, 1,2-phenylene, 1,3-phenylene, and 1,4-phenylene.

In a preferred embodiment, each of $L^a$ and $L^b$ is independently selected from alkylene groups of formula (3):

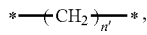
(3)

wherein n' is an integer having a value of 2 to 6. In another embodiment, $L^a$ and $L^b$ are 1,2-ethylene.

Exemplary non-limiting Q' groups include structures of formulas (4)-(7):

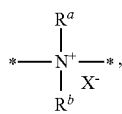
(4)

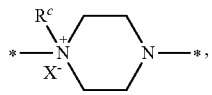
(5)

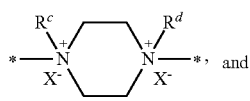
(6) and

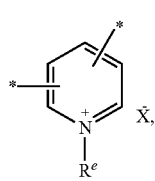
(7)

wherein $R^a$, $R^b$, $R^c$, $R^d$, $R^e$ are independent monovalent hydrocarbon groups comprising 1-20 carbons, and each $X^-$ is an independent negative-charged counterion.

Exemplary $R^a$, $R^b$, $R^c$, $R^d$, $R^e$ monovalent hydrocarbon groups include methyl, ethyl, n-propyl, isopropyl, n-butyl, sec-butyl, tert-butyl, n-pentyl, iso-pentyl, neo-pentyl, cyclopentyl, n-hexyl, cyclohexyl, and benzyl.

Exemplary negative-charged $X^-$ counterions include halides (e.g., fluoride, chloride, bromide, iodide), hydroxide, alkoxides, aryloxides, alkyl and aryl carboxylates (e.g., acetate, benzoate), hydrogen carbonate, alkyl and aryl sulfonates (e.g., methanesulfonate, p-toluenesulfonate), methyl sulfate, hydrogen sulfate, nitrate, dihydrogen phosphate, dialkyl and diaryl phosphates, and alkyl and aryl phosphonates.

The polyamine can comprise the cationic repeat units singularly or in combination.

More specific polyamines comprise a polymeric repeat unit of formula (8):

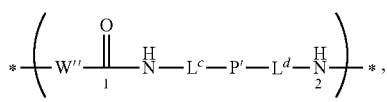
(8)

wherein

W" is a single bond or a divalent linking group having a structure *—C(=O)-L"-*, wherein L" is divalent radical comprising 1-20 carbons and L" is linked to carbonyl carbon 1, $L^c$ and $L^b$ are independent divalent linking groups selected from the group consisting of a single bond, and hydrocarbon groups comprising 1-6 carbons, and P' is a divalent poly(alkylene oxide) chain.

L" can be any of the above-described groups for L', and W" can be any of the above-described groups for W', where it should be understood that the atomic centers linked to carbonyl carbon 1 of formula (1) for W' are linked to carbonyl carbon 1 of formula (8) for W". In an embodiment, L" is the same as L' and W" is the same as W'.

$L^c$ and $L^d$ can be the same or different hydrocarbon groups. Exemplary non-limiting L and $L^d$ groups include 1,1-ethylene, 1,2-ethylene, 1,1-propylene, 1,2-propylene, 1,3-propylene, 1,1-butylene, 1,2-butylene, 1,3-butylene, 1,4-butylene, 1,1-pentylene, 1,2-pentylene, 1,3-pentylene, 1,4-pentylene, 1,5-pentylene, 1,2-cyclohexylene, 1,3-cyclohexylene, 1,4-cyclohexylene, 1,2-phenylene, 1,3-phenylene, and 1,4-phenylene. In an embodiment, $L^c$ is 1,2-propylene, wherein P' is linked to the 1 position of 1,2-propylene, and $L^d$ is a single bond. In another embodiment, L is 1,2-ethylene and $L^d$ is a single bond.

P' is a hydrophilic poly(alkylene) oxide chain comprising ethylene oxide and/or propylene oxide repeat units. P' can be a homopolymer of ethylene oxide (referred to as a PEG chain), or of propylene oxide units (referred to as a PPO chain). P' can be a random copolymer comprising ethylene oxide and propylene oxide repeat units. P' can be a block copolymer comprising 2 or more blocks comprising ethylene oxide and propylene oxide repeat units. For example, P' can be a diblock copolymer chain comprising a PEG block and a PPO block (denoted as *-PEG-b-PPO-*), wherein each block has an average degree of polymerization (DP) greater than 1. Alternatively, P' can be a triblock copolymer chain (e.g., *-PPO-b-PEG-b-PPO-* or *-PEG-b-PPO-b-PEG-*). One or more of the blocks of the block copolymer can be a random copolymer chain comprising ethylene oxide and propylene oxide repeat units (e.g., *-PPO-b-[PPO-r-PEO]-b-PEO-*, where the center block is a random copolymer chain).

A PEG chain has the structure:

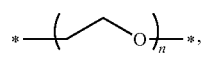

where n has an average value greater than 1.

A PPO chain has the structure:

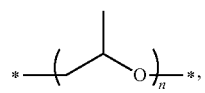

where n has an average value of greater than 1.

In an embodiment, P' has a triblock structure according to formula (9):

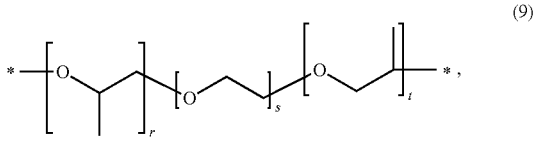

(9)

wherein r, s, and t represent degrees of polymerization of respective blocks of alkylene oxide repeat units enclosed in the brackets, r, s, and t independently have average values greater than 1.

In an embodiment, s/(r+t) has a value of about 2 to about 12.

P' can have a number average molecular weight of about 500 to about 5000. More specifically, P' can have a number average molecular weight of about 1500 to about 2500.

More specific polymeric repeat units have a structure according to formula (10):

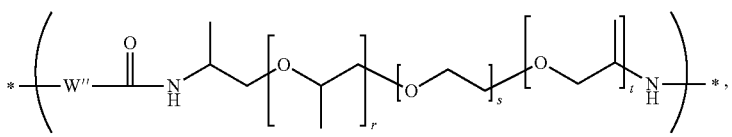

(10)

wherein

W" is a single bond or a divalent linking group having a structure *—C(=O)-L"-*, wherein L" is divalent radical comprising 1-20 carbons and L" is linked to carbon 1, r, s, and t represent average numbers of respective alkylene oxide repeat units, and r, s, and t independently have average values greater than 1.

The polyamine can comprise the polymeric repeat units singularly or in combination.

When present, the polymeric repeat unit is present in an amount of more than 0 mol % to about 10 mol % based on total moles of repeat units of the polyamine, wherein molecular weight of P' is based on number average molecular weight (Mn).

Preparation of Cationic Polyamides

The cationic polyamides are preferably prepared by a step-growth polymerization performed in bulk using a base organocatalyst (e.g., 1,8-diazabicycloundec-7-ene (DBU), 1,5-diazabicyclo(4.3.0)non-5-ene (DBN), 1,5,7-triazabicyclo[4.4.0]dec-5-ene (TBD)).

The reaction mixture contains a "carbonyl monomer". The carbonyl monomer can comprise a carbonate compound capable of reacting with two primary amine groups to form a urea. Exemplary non-limiting carbonyl monomers of this type include diethyl carbonate, diphenyl carbonate, and bis-pentafluorophenyl carbonate.

Other carbonyl monomers comprise two carbonyl groups in the form of carboxylic ester groups, carbonate groups, carbamate groups, or a combination thereof. In this instance, each of the two carbonyl groups of the carbonyl monomer is capable of reacting with a primary amine to form an amide, carbamate, or a urea group.

The reaction mixture also contains an amine monomer comprising two primary amine groups and a tertiary amine group. The tertiary amine group is capable of forming positive charged quaternary ammonium group in a reaction with an alkylating agent (quaternizing agent).

In a preferred embodiment, the reaction mixture also comprises a second reactive diamine comprising a poly (alkylene oxide) chain terminated at each end by a primary amine group. This reactant is referred to herein as the "polyether diamine".

The carbonyl monomer, the amine monomer, organocatalyst, and optionally the polyether diamine can be heated together without solvent at a temperature of about 100° C. to 200° C. in one or more heating stages to effect polymerization. The reaction time can vary from about 1 hour to about 24 hours. Optionally, vacuum can be applied to remove alcohol byproduct and assist in driving the reaction to completion. The bulk polymerization generates an initial polymer that can precipitate during the reaction.

Exemplary non-limiting amine monomers include those of formula (11):

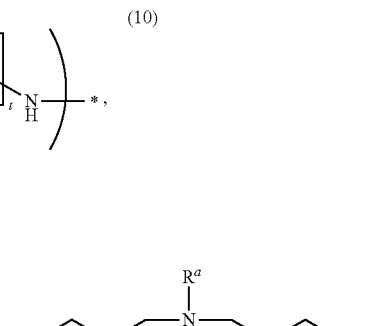

(11)

wherein $R^a$ is a monovalent hydrocarbon group comprising 1-20 carbons, and j and j' are independent integers having values of 0 to 18.

In an embodiment, $R^a$ is methyl, j is 1, and j' is 1 of formula (11).

Other amine monomers include those of formula (12):

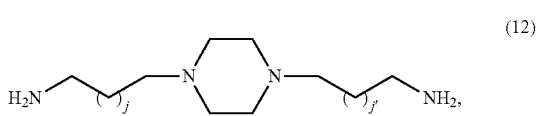

(12)

wherein j and j' are independent integers having values of 0 to 18.

In an embodiment, j is 1 and j' is 1 of formula (12).

Other amine monomers include those of formula (13):

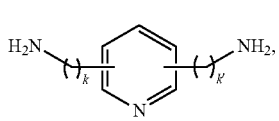

(13)

wherein k and k' are independent integers having values of 1 to 20.

The amine monomers can be used singularly or in combination.

No restriction is placed on carbonyl monomers comprising two carbonyl groups, with the proviso that the desirable properties of the cationic polyamine are not adversely affected (biodegradability, antimicrobial activity, hemolysis, and cytotoxicity) by the structure of the carbonyl monomer. The carbonyl monomers can be used singularly or in combination.

Carbonyl monomers comprising two carbonyl groups include diester monomers such as, for example, dimethyl malonate, diethyl malonate, diethyl 2-methylmalonate, diethyl 2-propylmalonate, diethyl 2-iso-propylmalonate, diethyl 2-n-butylmalonate, dimethyl isobutylmalonate, 2-tert-butylmalonate, diethyl 2-pentylmalonate, diethyl 2-heptylmalonate, diethyl 2-hexylmalonate, dimethyl succinate, diethyl succinate, dimethyl glutarate, diethyl glutarate, dimethyl adipate, diethyl adipate, dimethyl pimelate, diethyl pimelate, diethyl 1,1-cyclohexanedicarboxylate, diethyl 1,4-cyclohexanedicarboxylate, dimethyl terephalate, dimethyl isophthalate. The diester monomer can comprise alkyl esters, aryl esters, and combinations thereof.

Exemplary non-limiting carbonyl monomers comprising two carbamate groups include compounds of formula (13):

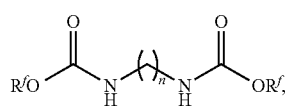

(13)

wherein n is an integer having a value of 2-20, and each $R^f$ is selected from the group consisting of methyl, ethyl, t-butyl, and phenyl.

Each hydrogen of the methylene groups enclosed in parentheses of formula (13) can optionally be substituted with an alkyl or aryl substituent (e.g., methyl, ethyl, or phenyl).

Other non-limiting carbonyl monomers comprising two carbamate groups include compounds of formula (14):

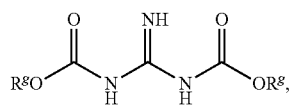

(14)

wherein each $R^g$ is selected from the group consisting of methyl, ethyl, t-butyl, and phenyl.

In an embodiment, each R of formula (14) is t-butyl.

Exemplary non-limiting carbonyl monomers comprising two carbonate groups include ethylene glycol bis(2-chloro-4-nitrophenyl carbonate), propylene glycol bis(2-chloro-4-nitrophenyl carbonate), butylene glycol bis(2-chloro-4-nitrophenyl carbonate), and 1,4-butylene glycol bis(2-chloro-4-nitrophenyl carbonate), diethylene glycol bis(2-chloro-4-nitrophenyl carbonate), dipropylene glycol bis(2-chloro-4-nitrophenyl carbonate), dibutylene glycol bis(2-chloro-4-nitrophenyl carbonate), triethylene glycol bis(2-chloro-4-nitrophenyl carbonate), tripropylene glycol bis(2-chloro-4-nitrophenyl carbonate), tributylene glycol bis(2-chloro-4-nitrophenyl carbonate), tetraethylene glycol bis(2-chloro-4-nitrophenyl carbonate, tetrabutylene glycol bis(2-chloro-4-nitrophenyl carbonate), pentapropylene glycol bis (2-chloro-4-nitrophenyl carbonate), and octaethylene glycol bis(2-chloro-4-nitrophenyl carbonate). The 2-chloro-4-nitrophenyl groups of each of the foregoing compounds can be replaced with any suitable activating group such as, for example, p-nitrophenyl, pentachlorophenyl, pentafluorophenyl, and the like.

The carbonyl monomers can be used singularly or in combination.

The polyether diamine has a structure in accordance with formula (15):

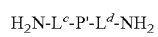

$H_2N-L^c-P'-L^d-NH_2$ (15), wherein $L^c$ and $L^d$ are independent divalent linking groups selected from the group consisting of a single bond, and hydrocarbon groups comprising 1-6 carbons, and P' is a divalent poly(alkylene oxide) chain.

P' can be a homopolymer, random copolymer, or block copolymer comprising alkylene oxide repeat units. Especially preferred alkylene oxides units are ethylene oxide and propylene oxide.

Exemplary non-limiting polyether diamines include diamine terminated triblock copolymers poly(propylene oxide)-block-poly(ethylene oxide)-block-poly(propylene oxide):

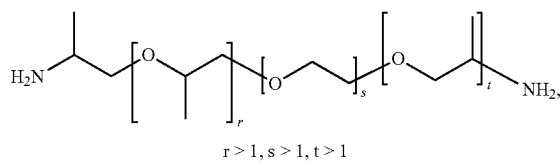

r > 1, s > 1, t > 1 diamine terminated homopolymers of propylene oxide:

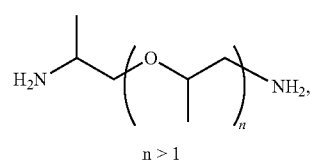

n > 1 diamine terminated homopolymers of ethylene oxide:

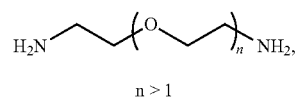

n > 1 and diamine terminated random copolymers of ethylene oxide and propylene oxide represented by formula (16):

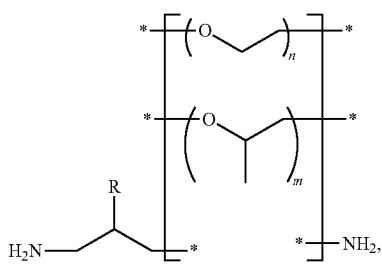

(16)

wherein n represents the average number of ethylene oxide repeat units, m represents the average number of propylene oxide repeat units, each of n and m has an average value greater than 1, and R is H or methyl.

In the above notation, the stacking of repeat units within the square brackets represents a random distribution of the repeat units in the polymer chain. The starred bonds of each repeat unit overlapping the left bracket can be bonded to a different repeat unit at an attachment point indicated by the starred bonds of the repeat units overlapping the right square bracket, or to the end group represented by the structure $H_2N-C(R)CH_2-$*. Likewise, the starred bonds of the repeat units overlapping the right bracket can be bonded to a different repeat unit at an attachment point indicated by the starred bonds of the repeat units overlapping the right square bracket, or to an end group represented by *—$NH_2$. Subscripts n and m represent independent average numbers of respective repeat units enclosed in the parentheses. The polyether diamines can be used singularly or in combination.

A polyether diamine can have a number average molecular weight (Mn) of about 500 to about 5000. A polyether diamine can have a weight average molecular weight (Mw) of about 1000 to about 25000.

Quaternization

The initial polymer formed is treated with a suitable nitrogen quaternizing agent to convert the tertiary amine groups of the initial polymer to positive charged quaternary ammonium groups. The quaternizing agent can be any suitable material. such as, for example, an alkyl halide, alkyl sulfonate, and/or benzyl halide. The quaternizing agents can be used singularly or in combination. In an embodiment, the quaternizing agent is methyl iodide and/or benzyl bromide.

Molecular Weight

The polyamines can have a number average molecular weight (Mn) of about 700 to about 25000. The polyamines can have a weight average molecular weight (Mw) of about 1000 to about 50000.

Antimicrobial Properties

For the examples further below, the following definitions are applicable.

HC50 is defined as the concentration (in mg/L) of cationic polyamine that causes 50% of mammalian red blood cells to undergo hemolysis. HC50 values of 1000 mg/L or higher are desirable.

HC20 is defined as the concentration (in mg/L) of cationic polyamine that causes 20% of mammalian red blood cells to undergo hemolysis. HC20 values of 500 mg/L or higher are desirable.

Minimum inhibitory concentration (MIC) is defined as the minimum concentration (in mg/L) of cationic polyamine required to inhibit growth of a given microbe for an 18 hour period (bacteria) or 42 hour period (fungi). A MIC less than 500 mg/L is desirable. Even more desirable is a MIC of 150 mg/L or less. A lower MIC indicates higher antimicrobial activity.

Minimum bactericidal concentration (MBC) is defined as the minimum concentration (in mg/L) of cationic polyamine required to kill a given microbe. A lower MBC indicates higher antimicrobial activity.

HC50 selectivity is defined as the ratio of HC50/MIC. An HC50 selectivity of 3 or more is desirable. Higher HC50 selectivity values indicate more activity against bacterial cells and less toxicity to mammalian cells. Likewise, HC20 selectivity is defined as the ratio of HC20/MIC. An HC20 selectivity of 3 or more is desirable.

Non-limiting exemplary bacteria include Gram-positive *Staphylococcus aureus* (*S. aureus*), Gram-negative *Escherichia coli* (*E. coli*), fungus *Candida albicans* (*C. albicans*), Gram-negative *Pseudomonas aeruginosa* (*P. aeruginosa*), and yeasts. Other microbes include Gram-positive *Staphylococcus epidermidis* (*S. epidermidis*), Gram-positive Methicillin-resistant *Staphylococcus aureus* (MRSA), Gram-positive Vancomycin-resistant *Enterococcus* (VRE), Gram-negative *Acinetobacter baumannii* (*A. baumannii*), and Gram-negative *Klebsiella pneumoniae* (*K. pneumoniae*) and *Cryptococcus neoformans* (*C. neoformans*).

The polyamines can have a minimum inhibitory concentration (MIC) of about 8 mg/L to about 500 mg/L, and more preferably about 8 mg/L to about 250 mg/L, and most preferably 8 mg/L to about 125 mg/L against a bacterium. In an embodiment, the cationic polyamines can have a MIC of about 8 mg/L to about 63 mg/L against *P. aeruginosa*.

The cationic polyamines can exhibit less than about 50% hemolysis at 1000 mg/L (i.e., can have an HC50 value greater than 1000 mg/L).

The repeat unit comprising the poly(alkaline oxide) chain, when present, can substantially improve skin cell viability at concentrations higher than MIC without adversely affecting microbial toxicity.

INDUSTRIAL APPLICABILITY

The cationic polyamines have utility as antimicrobial components of consumer products that are used in contact with skin such as, for example, cosmetics (e.g., skin lotions, skin creams, topically applied powders, mascara, eye liners, lip glosses), soaps, shampoos, and deodorants. The cationic polyamines also have utility as antimicrobial components of laundry detergents.

The cationic polyamines also have utility for human and/or non-human therapeutic medical treatments. The polyamines can be used in the form of a stand-alone antibiotic drug and/or as a complex comprising the polyamine and an anionic form of biologically active material (e.g., genes, drugs) bound by non-covalent interactions. A medical composition comprising the polyamine and/or a biologically active material selected from the group consisting of genes, drugs, and combinations thereof, can be administered topically, intravenously, orally, by way of other body cavities, and/or by inhalant. The medical composition can have the form of a powder, a pill, a liquid, a paste, or a gel. The medical compositions are particularly attractive for use in injectable systems for delivery of rigid, hydrophobic biologically active materials that have low water solubility, such as the drugs paclitaxel and doxorubicin.

A method comprises contacting a microbe with a polyamine, thereby killing the microbe.

Another method comprises contacting a tumor cell with a complex comprising a disclosed polyamine and a tumor-treating drug, thereby killing the tumor cell.

An antimicrobial composition comprises a disclosed polyamine and at least one other component (e.g., water, drug, gene). The antimicrobial composition can be applied to a human and/or non-human animal tissue, including mammalian and/or non-mammalian animal tissue. The general term "animal tissue" includes wound tissue, burn tissue, skin, internal organ tissue, blood, bones, cartilage, teeth, hair, eyes, nasal surfaces, oral surfaces, other body cavity surfaces, and any cell membrane surfaces. In an embodiment, a method comprises contacting an animal tissue with the antimicrobial composition, thereby inhibiting, preventing, and/or eradicating a microbial infection of the tissue.

Other uses of the polyamines include disinfectant washes for hands, skin, hair, bone, ear, eye, nose, throat, internal tissue, wounds, and teeth (e.g., as a mouthwash).

Still other uses of the polyamines include disinfectants for articles such as medical devices. Medical devices include swabs, catheters, sutures, stents, bedpans, gloves, facial masks, absorbent pads, absorbent garments, internal absorbent devices, and insertable mechanical devices. In an embodiment, a method comprises contacting a medical device with an antimicrobial composition comprising a disclosed polyamine, thereby disinfecting the medical device. In an embodiment, the medical device is a catheter.

The antimicrobial compositions are also attractive as disinfecting agents for surfaces of articles (i.e., non-living articles) such as, for example, building surfaces in homes, businesses, and particularly hospitals. Exemplary home and commercial building surfaces include floors, door surfaces, bed surfaces, air conditioning surfaces, bathroom surfaces, railing surfaces, kitchen surfaces, and wall surfaces. Other articles include medical devices, cloths, garments, and non-medical equipment. Surfaces of articles can comprise materials such as wood, paper, metal, cloth, plastic, rubber, glass, paint, leather, or combinations thereof. In an embodiment, a method comprises contacting a surface of an article with an antimicrobial composition comprising a disclosed polyamine, thereby disinfecting the surface. In another embodiment, the antimicrobial composition has the form of a solution.

In an embodiment, the antimicrobial composition is selected from the group consisting of soaps, shampoos, skin lotions, skin creams, cosmetics, mouthwashes, wound care agents, deodorants, surface cleaning agents, and laundry detergents.

Polyamine Complexes

In water, optionally containing organic solvent, the polyamines can form a nanoparticulate complex with an anionic biologically active cargo material, bound by non-covalent interactions. These "loaded" complexes can have the form of a micelle that comprises a plurality of self-assembled macromolecules of the polyamine and one or more molecules of the cargo material encapsulated therein.

A method of forming a nanoparticulate polyamine complex comprises i) forming a first solution comprising a polyamine (i.e., carrier) and water; ii) forming a second solution comprising a biologically active material (i.e., cargo) in water and/or a water miscible organic solvent; iii) combining the first and seconds solutions; and iv) removing any organic solvent (e.g., by dialysis), thereby forming an aqueous mixture comprising the complex. The complex can comprise the polyamine in an amount of 85.0 wt. % to 99.9 wt. %, and the biologically active material in an amount of about 15.0 wt. % to 0.1 wt. %, each based on total dry solids weight of the complex.

The term "loading efficiency" refers to the percentage of the initial weight of the biologically active material that is incorporated into the polyamine complex. The loading efficiency of the biologically active material in the polyamine complex is preferably at least 10%. Generally, the loading efficiency of the biologically active material is in a range of 10% to 50%, and even more specifically in a range of 30% to 50%.

Nanoparticles of the polyamine complex can have an average particle size (circular cross sectional diameter) of 10 nm to 500 nm, 10 nm to 250 nm, and preferably 25 nm to 200 nm as measured by dynamic light scattering. For the foregoing particle sizes, the aqueous solution can have a pH of 4.5 to 8.0, 5.0 to 7.0, or 6.0 to 7.0.

The organic solvent, if any, used to prepare the polyamine complex is preferably miscible with water at concentrations of at least 1 microliter or more of organic solvent per 100 microliters of water. Exemplary organic solvents include methanol, ethanol, propanol, 2-propanol, 1-butanol, 2-butanol, t-butyl alcohol, acetone, 2-butanone, dimethoxyethane, diglyme, diethyl ether, methyl t-butyl ether, methylene chloride, ethyl acetate, ethylene glycol, glycerin, dimethylsulfoxide, dimethylformamide, acetic acid, tetrahydrofuran (THF), and dioxane.

As stated above, the biologically active cargo material can be a drug. Exemplary commercially available drugs include the following, where the generic drug is enclosed in parentheses: 13-cis-Retinoic Acid, 2-CdA (Cladribine), 2-Chlorodeoxyadenosine (Cladribine), 5-Azacitidine, 5-Fluorouracil (Fluorouracil), 5-FU (Fluorouracil), 6-Mercaptopurine, 6-MP (6-Mercaptopurine), 6-TG (Thioguanine), 6-Thioguanine (Thioguanine), ABRAXANE® (Paclitaxel protein bound), ACCUTANE® (Isotretinoin), Actinomycin-D (Dactinomycin), ADRIAMYCIN® (Doxorubicin), ADRUCIL® (Fluorouracil), AFINITOR® (Everolimus), AGRYLIN® (Anagrelide), ALA-CORT® (Hydrocortisone), Aldesleukin, Alemtuzumab, ALIMTA® (Pemetrexed), Alitretinoin (9-cis-retinoic acid), Alkaban-AQ (Vinblastine), ALKERAN® (Melphalan), All-transretinoic Acid (Tretinoin), Alpha Interferon (Interferon Alfa), Altretamine, Amethopterin (Methotrexate), Amifostine, Aminoglutethimide, Anagrelide, ANANDRON® (Nilutamide), Anastrozole, Arabinosylcytosine (Cytarabine), Ara-C(Cytarabine), ARANESP® (Darbepoetin Alfa), AREDIA® (Pamidronate), ARIMIDEX® (Anastrozole), AROMASIN® (Exemestane), ARRANON® (Nelarabine), Arsenic Trioxide, Asparaginase, ATRA (All-transretinoic Acid), AVASTIN® (Bevacizumab), Azacitidine, BCG, BCNU (Carmustine), Bendamustine (Bendamustine Hydrochloride), Bevacizumab, Bexarotene, BEXXAR® (Tositumomab), Bicalutamide, BICNU® (Carmustine), BLENOXANE® (Bleomycin), Bleomycin, Bortezomib, Busulfan, BUSULFEX® (Busulfan), C225 (Cetuximab), Calcium Leucovorin (Leucovorin), CAMPATH® (Alemtuzumab), CAMPTOSAR® (Irinotecan), Camptothecin-11 (Irinotecan), Capecitabine, CARAC® (Fluorouracil), Carboplatin, Carmustine, Carmustine Wafer, CASODEX® (Bicalutamide), CC-5013 (Lenalidomide), CCI-779 (Temsirolimus), CCNU (Lomustine), CDDP (Cisplatin), CEENU® (Lomustine), CERUBIDINE® (Daunomycin), Cetuximab, Chlorambucil, Cisplatin, Citrovorum Factor (Leucovorin), Cladribine, Cortisone (Hydrocortisone), COSMOGEN® (Dactinomycin), CPT-11 (Irinotecan), Cyclophosphamide, CYTADREN® (Aminoglutethimide), Cytarabine, Cytarabine Liposomal, CYTOSAR-U® (Cytarabine), CYTOXAN® (Cyclophosphamide), Dacarbazine, DACOGEN® (Decitabine), Dactinomycin, Darbepoetin Alfa, Dasatinib, Daunomycin, Daunorubicin, Daunorubicin Hydrochloride, Daunorubicin Liposomal, DAUNOXOME® (Daunorubicin Liposomal), DECADRON™ (Dexamethasone), Decitabine, DELTA-CORTEF® (Prednisolone), DELTASONE® (Prednisone), Denileukin Diftitox, DEPOCYT® (Cytarabine Liposomal), Dexamethasone, Dexamethasone Acetate, Dexamethasone Sodium Phosphate, DEXASONE® (Dexamethasone), Dexrazoxane, DHAD (Mitoxantrone), DIC (Dacarbazine), DIODEX® (Dexamethasone), Docetaxel, DOXIL® (Doxorubicin Liposomal), Doxorubicin, Doxorubicin Liposomal, DROXIA® (Hydroxyurea), DTIC (Dacarbazine), DTIC-DOME® (Decarbazine), Duralone (Methylprednisolone), EFUDEX® (Fluorouracil), ELIGARD® (Leuprolide), ELLENCE® (Epirubicin), ELOXATIN® (Oxaliplatin), ELSPAR® (Asparaginase), EMCYT® (Estramustine), Epirubicin, Epoetin Alfa, ERBITUX® (Cetuximab), Erlotinib, Erwinia L-asparaginase (Asparaginase), Estramustine, ETHYOL® (Amifostine), ETOPOPHOS® (Etoposide), Etoposide, Etoposide Phosphate, EULEXIN® (Flutamide), Everolimus, EVISTA® (Raloxifene), Exemestane, FARESTON® (Toremifene), FASLODEX® (Fulvestrant), FEMARA® (Letrozole), Filgrastim, Floxuridine, FLUDARA® (Fludarabine), Fludarabine, FLUOROPLE® (Fluorouracil), Fluorouracil, Fluorouracil (cream), Fluoxymesterone, Flutamide, Folinic Acid (Leucovorin), FUDR® (Floxuridine), Fulvestrant, G-CSF (Pegfilgrastim), Gefitinib, Gemcitabine, Gemtuzumab ozogamicin, GEMZAR® (Gemcitabine), GLEEVEC® (Imatinib mesylate), GLIADEL® Wafer (Carmustine Wafer), GM-CSF (Sargramostim), Goserelin, Granulocyte—Colony Stimulating Factor (Pegfilgrastim), Granulocyte Macrophage Colony Stimulating Factor (Sargramostim), HALOTESTIN® (Fluoxymesterone), HERCEPTIN® (Trastuzumab), HEXADROL® (Dexamethasone), HEXALEN® (Altretamine), Hexamethylmelamine (Altretamine), HMM (Altretamine), HYCAMTIN® (Topotecan), HYDREA® (Hydroxyurea), Hydrocort Acetate (Hydrocortisone), Hydrocortisone, Hydrocortisone Sodium Phosphate, Hydrocortisone Sodium Succinate, HYDROCORTONE® Phosphate (Hydrocortisone), Hydroxyurea, Ibritumomab, Ibritumomab Tiuxetan (Ibritumomab), IDAMYCIN® (Idarubicin), Idarubicin, IFEX® (Ifosfamide), IFN-alpha (Interferon alfa), Ifosfamide, IL-11 (Oprelvekin), IL-2 (Aldesleukin), Imatinib mesylate, Imidazole Carboxamide (Decarbazine), Interferon alfa, Interferon Alfa-2b (PEG Conjugate), Interleukin-2 (Aldesleukin), Interleukin-11 (Oprelvekin), INTRON® A (interferon alfa-2b), IRESSA® (Gefitinib), Irinotecan, Isotretinoin, Ixabepilone, IXEMPRA® (Ixabepilone), Kidrolase (Asparaginase), LANACORT® (Hydrocortisone), Lapatinib, L-asparaginase, LCR (Vincristine), Lenalidomide, Letrozole, Leucovorin, LEUKERAN® (Chlorambucil), LEUKINE® (Sargramostim), Leuprolide, Leurocristine (Vincristine), LEUSTATIN® (Cladribine), Liposomal Ara-C, LIQUID PRED® (Prednisone), Lomustine, L-PAM (Melphalen), L-Sarcolysin (Melphalen), LUPRON® (Leuprolide), LUPRON DEPOT® (Leuprolide), MATULANE® (Procarbazine), MAXIDEX® (Dexamethasone), Mechlorethamine, Mechlorethamine Hydrochloride, Medralone (Methylprednisolone), MEDROL® (Methylprednisolone), MEGACE® (Megestrol), Megestrol, Megestrol Acetate (Megastrol), Melphalan, Mercaptopurine (6-Mercaptopurine), Mesna, MESNEX® (Mesna), Methotrexate, Methotrexate Sodium (Methotrexate), Methylprednisolone, METICORTEN® (Prednisone), Mitomycin (Mitomycin C), Mitomycin-C, Mitoxantrone, M-Prednisol (Methylprednisolone), MTC (Mitomycin-C), MTX (Methotrexate), MUSTARGEN® (Mechlorethamine), Mustine (Mechlorethamine), MUTAMYCIN® (Mitomycin-C), MYLERAN® (Busulfan), MYLOCEL® (Hydroxyurea), MYLOTARG® (Gemtuzumab ozogamicin), NAVELBINE® (Vinorelbine), Nelarabine, NEOSAR® (Cyclophosphamide), NEULASTA® (Pegfilgrastim), NEUMEGA® (Oprelvekin), NEUPOGEN® (Filgrastim), NEXAVAR® (Sorafenib), NILANDRON® (Nilutamide), Nilutamide, NIPENT® (Pentostatin), Nitrogen Mustard (Mechlorethamine), NOLVADEX® (Tamoxifen), NOVANTRONE® (Mitoxantrone), Octreotide, Octreotide acetate (Octreotide), ONCASPAR® (Pegaspargase), ONCOVIN® (Vincristine), ONTAK® (Denileukin Diftitox), ONXOL® (Paclitaxel), Oprelvekin (Interleukin-11), ORAPRED® (Prednisolone), ORASONE® (Prednisone), Oxaliplatin, Paclitaxel, Paclitaxel Protein-bound, Pamidronate, Panitumumab, PANRETIN® (Alitretinoin), PARAPLATIN® (Carboplatin), PEDIAPRED® (Prednisolone), PEG Interferon, Pegaspargase, Pegfilgrastim, PEG-INTRON® (Interferon Alfa-2b), PEG-L-asparaginase, Pemetrexed, Pentostatin, Phenylalanine Mustard (Melphalen), PLATINOL® (Cisplatin), Platinol-AQ (Cisplatin), Prednisolone, Prednisone, PRELONE® (Prednisolone), Procarbazine, PROCRIT® (Epoetin Alfa), PROLEUKIN® (Aldesleukin), Prolifeprospan 20 with Carmustine Implant (Carmustine Wafer), PURINETHOL® (6-Mercaptopurine), Raloxifene, REVLIMID® (Lenalidomide), RHEUMATREX® (Methotrexate), RITUXAN® (Rituximab), Rituximab, Roferon-A (Interferon Alfa-2a), RUBEX® (Doxorubicin), Rubidomycin hydrochloride (Daunomycin), SANDOSTATIN® (Octreotide), SANDOSTATIN LAR® (Octreotide), Sargramostim, SOLU-CORTEF® (Hydrocortisone), SOLU-MEDROL® (Methylprednisolone), Sorafenib, SPRYCEL® (Dasatinib), STI-571 (Imatinib Mesylate), Streptozocin, SU11248 (Sunitinib), Sunitinib, SUTENT® (Sunitinib), Tamoxifen, TARCEVA® (Erlotinib), TARGRETIN® (Bexarotene), TAXOL® (Paclitaxel), TAXOTERE® (Docetaxel), TEMODAR® (Temozolomide), Temozolomide, Temsirolimus, Teniposide, TESPA (Thiotepa), Thalidomide, THALOMID® (Thalidomide), THERACYS® (BCG), Thioguanine, Thioguanine Tabloid (Thioguanine), Thiophosphoamide (Thiotepa), THIOPLEX® (Thiotepa), Thiotepa, TICE® (BCG), TOPOSAR® (Etoposide), Topotecan, Toremifene, TORISEL® (Temsirolimus), Tositumomab, Trastuzumab, TREANDA® (Bendamustine Hydrochloride), Tretinoin, TREXALL® (Methotrexate), TRISENOX® (Arsenic Trioxide), TSPA (Thiotepa), TYKERB® (Lapatinib), VCR (Vincristine), VECTIBIX® (Panitumumab), VELBAN® (Vinblastine), VELCADE® (Bortezomib), VEPESID® (Etoposide), VESANOID® (Tretinoin), VIADUR® (Leuprolide), VIDAZA® (Azacitidine), Vinblastine, Vinblastine Sulfate, VINCASAR PFS® (Vincristine), Vincristine, Vinorelbine, Vinorelbine tartrate (Vinorelbine), VLB (Vinblastine), VM-26 (Teniposide), Vorinostat, VP-16 (Etoposide), VUMON® (Teniposide), XELODA® (Capecitabine), ZANOSAR® (Streptozocin), ZEVALIN® (Ibritumomab), ZINECARD® (Dexrazoxane), ZOLADEX® (Goserelin), Zoledronic acid, ZOLINZA® (Vorinostat), and ZOMETA® (Zoledronic acid).

The following examples demonstrate the preparation, antimicrobial properties, hemolytic properties, and cytotoxicity of the polyamines.

EXAMPLES

Materials used in the following examples are listed in Table 1.

TABLE 1

| ABBREVIATION | DESCRIPTION | SUPPLIER |
|---|---|---|
| BAPPIP | 1,4-Bis(3-aminopropyl)piperazine | Sigma-Aldrich |
| BnBr | Benzyl bromide | Sigma-Aldrich |
| DAMDPA | 3,3'- diamino-N-methyldipropylamine | Sigma-Aldrich |
| DBocG | Di-boc-guanidine | Sigma-Aldrich |
| DEC | Diethyl carbonate | Sigma-Aldrich |
| DESucc | Diethyl succinate | Sigma-Aldrich |
| DMEM | Dulbecco's Modified Eagle Medium | Invitrogen |
| DMM | Dimethyl 2-methylmalonate | Sigma-Aldrich |
| DMS | Dimethyl sulfate | Sigma-Aldrich |
| ED-2003 | Triblock copolymer O,O'-Bis(2-aminopropyl) polypropylene glycol-block-polyethylene glycol-block-polypropylene glycol; JEFFAMINE; Mn 1900 | Sigma-Aldrich |
| FBS | Fetal Bovine Serum | Invitrogen |
| HDF | Human dermal fibroblasts | ATCC, USA |
| HexBr | n-Hexyl bromide | Sigma-Aldrich |
| MDEA | N-methyldiethanolamine | Sigma-Aldrich |
| MHB | Mueller Hinton Broth | BD Diagnostics, SG |
| MTT | 3-[4,5-Dimenthylthiazol-2-yl]-2,5-diphenyl tetrazolium bromide | Invitrogen |
| PBS | Phosphate Buffered Saline | 1$^{st}$ Base, SG |
| TBD | 1,5,7-Triazabicyclo[4.4.0]dec-5-ene | Sigma-Aldrich |
| TSB | Tryptic Soy Broth | BD Diagnostics, SG |
| YMB | Yeast Mold Broth | BD Diagnostics, SG |

Herein, Mn is the number average molecular weight, Mw is the weight average molecular weight, and MW is the molecular weight of one molecule.

$^1$H NMR spectra were acquired on a Bruker Avance 400 instrument at 400 MHz. Gel permeation chromatography (GPC) was performed in tetrahydrofuran (THF) using a Waters system equipped with four 5-micrometer Waters columns (300 mm×7.7 mm) connected in series with increasing pore size (100, 1000, 105, and 106 angstroms), a Waters 410 differential refractometer, and a 996 photodiode array detector. The system was calibrated using polystyrene standards. GPC analysis was also performed in N,N-dimethylformamide (DMF) spiked with 0.01 M LiBr using a Waters system equipped with two Agilent PolyPore columns (300 mm×7.5 mm) connected in series, a Waters 410 differential refractometer. The system was calibrated with poly(methyl methacrylate) standards. GPC analysis was also performed in 54/23/23 (v/v/v %) water/methanol/acetic acid (H$_2$O/MeOH/AcOH) with 0.5 M sodium acetate (NaOAc) using a Waters system equipped with two Agilent PolyPore columns (300 mm×7.5 mm) connected in series, a Waters 410 differential refractometer. The system was calibrated with poly(ethylene oxide) standards.

All chemical reagents were purchased from Sigma-Aldrich, U.S.A. and used as received unless otherwise specified. Tryptic Soy Broth (TSB), Yeast Mold Broth (YMB) and Muller Hinton Broth (MHB) powder were purchased from BD Diagnostics (Singapore) and used to prepare the microbial broths according to the manufacturer's instruction. Cell lines of human dermal fibroblasts (HDF), *Staphylococcus aureus* (ATCC No. 6538, *S. aureus*), *Escherichia coli* (ATCC No. 25922, *E. coli*), *Pseudomonas aeruginosa* (ATCC No. 9027, *P. aeruginosa*), and *Candida albicans* (ATCC No 10231, *C. albicans*) were obtained from ATCC, U.S.A., and reconstituted according to the suggested protocols. Fetal bovine serum (FBS) was purchased from Invitrogen Corporation. 3-[4,5-Dimenthylthiazol-2-yl]-2,5-diphenyl tetrazolium bromide (MTT) was dissolved in phosphate-buffered saline (PBS, pH 7.4) with a concentration of 5 mg/mL, and the solution was filtered with a 0.22 micron filter to remove blue formazan crystals prior to usage. Rat red blood cells (RBCs) were obtained from the Animal Handling Unit of Biomedical Research Centers (Singapore).

Synthesis

The P31 series of polymers, P31a-d, was prepared according to the following reaction diagram, where n represents the average number of repeat units enclosed in the parentheses.

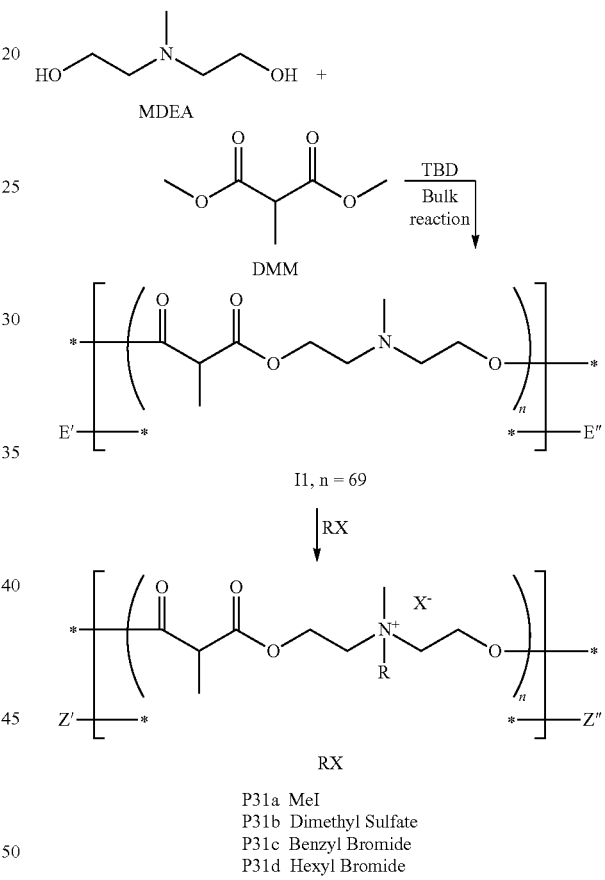

P31a MeI
P31b Dimethyl Sulfate
P31c Benzyl Bromide
P31d Hexyl Bromide

Example 1

Preparation of polymer P31a. N-methyldiethanolamine (MDEA, 0.68 g, 0.0057 mol), dimethyl 2-methylmalonate (DMM, 0.99 g, 0.0057 mol) and TBD (0.05 g, 0.00035 mol) were charged in a Schlenk tube. The reactants were mixed by simple vortex until miscible (1-2 minutes). The Schlenk tube was placed in a heated sand bath at 80° C. After about 4 hours, vacuum was applied to pull off the bi-product and shift the equilibrium towards product. The reaction was allowed to continue for another 20 hours. The intermediate polymer I1 crystallized, limiting the molecular weight. Mn (GPC, DMF=14000 g/mol, PDI=1.23, n=69 based on Mn). In the above structure of I1, E' and E" are end groups.

Potential E' groups of polymer I1 include MeO—* and

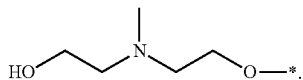

Potential E" groups of polymer I1 include: *—H and

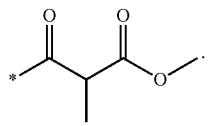 [SMILES: *C(=O)C(C)C(=O)OC]

Intermediate polymer I1 was dissolved in DMF (up to 100° C.), and once dissolved was separated into 4 vials (~0.5 g in DMF (8-10 ml)). One of samples was quaternized (50° C., 24 hours) with methyl iodide (0.5 g, 1.5 eq. (equivalents)). The polymer P31a was isolated by precipitation in diethyl ether. The polymer P31a was rinsed 3 times with diethyl ether and further purified via dialysis.

Example 2

P31b was prepared by charging one of the sample vials containing polymer I1 with dimethyl sulfate (DMS, 0.5 g, 1.5 eq.) following the general procedure above for P31a.

Example 3

P3c was prepared by prepared by charging one of the sample vials containing polymer I1 with benzyl bromide (BnBr, 0.6 g, 1.5 eq.) following the general procedure above for P31a.

Example 4

P3 d was prepared by prepared by charging one of the sample vials containing polymer I1 with hexyl bromide (HexBr, 0.6 g, 1.5 eq.) following the general procedure above for P31a.

In the above structures of P31a-d, Z' and Z" are end groups. Potential Z' groups of the P31a-d polymers include MeO—* and

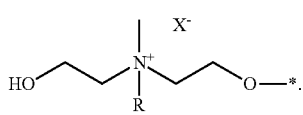

Potential Z" groups of the P31a-d polymers include *—H, the R group of RX, and

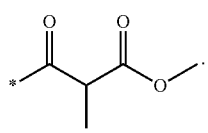 [SMILES: *C(=O)C(C)C(=O)OC]

Polymers P32a-d were prepared according to the following reaction diagram, where n and represents the average number of repeat units enclosed in the parentheses, and n=95.

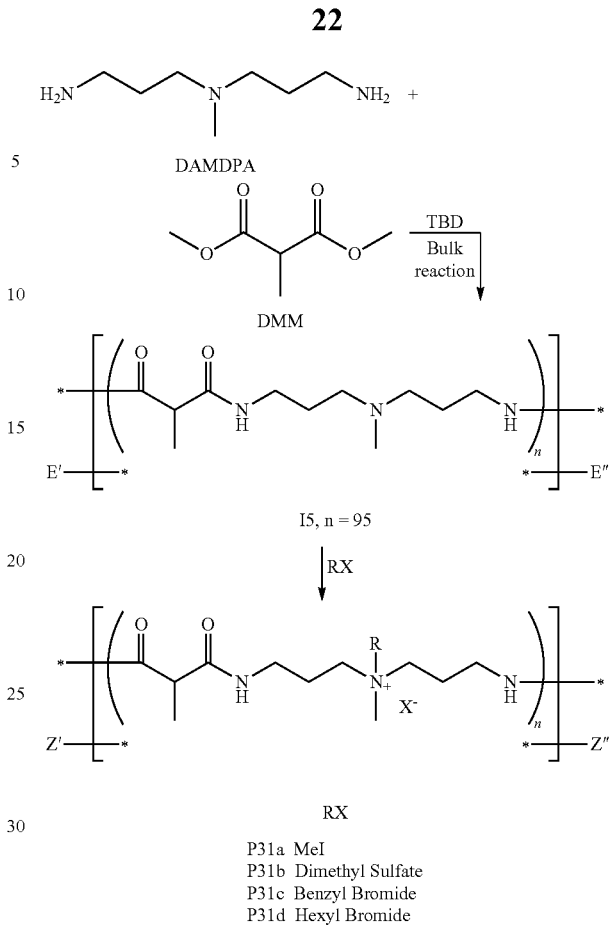

| | RX |
|---|---|
| P31a | MeI |
| P31b | Dimethyl Sulfate |
| P31c | Benzyl Bromide |
| P31d | Hexyl Bromide |

Example 5

Preparation of P32a. 3,3'-Diamino-N-methyldipropylamine (DAMDPA, 0.98 g, 0.0066 mol), DMM (1.14 g, 0.0066 mol) and TBD (0.05 g, 0.00035 mol) were charged in a Schlenk tube. The reactants were mixed by simple vortex until miscible (1-2 min). The Schlenk tube was placed in a heated sand bath at 80° C. After about 4 hours, vacuum was applied to remove the methanol byproduct and shift the equilibrium towards product. The reaction was allowed to continue for another 20 hours. The intermediate polymer I5 crystallized, thereby limiting the molecular weight. Mn (GPC, DMF=21600 g/mol, PDI=1.43, n=95 based on Mn).

Potential E' end groups of I5 include MeO—* and

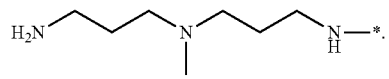

Potential E" end groups of I5 include *—H and

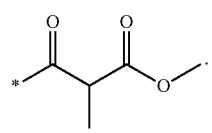

Intermediate polymer I5 was dissolved in DMF (up to 100° C.), and once dissolved was separated into vials (~0.5 g in DMF (8-10 ml)). One of the samples was quaternized (90° C., 24 hours) with methyl iodide (0.5 g, 1.5 eq.), forming P32a. The polymer P32a was isolated by precipitation in diethyl ether. The polymer P32a (n=95) was rinsed 3 times with diethyl ether and further purified via dialysis.

Example 6

P32b (n=95) was prepared by charging one of the sample vials containing polymer I5 with dimethyl sulfate (DMS, 0.5 g, 1.5 eq.) following the general procedure above for P32a.

Example 7

P32c (n=95) was prepared by prepared by charging one of the sample vials containing polymer I5 with benzyl bromide (BnBr, 0.6 g, 1.5 eq.) following the general procedure above for P32a.

Example 8

P32d (n=95) was prepared by prepared by charging one of the sample vials containing polymer I5 with hexyl bromide (HexBr, 0.6 g, 1.5 eq.) following the general procedure above for P32a.

Potential Z' end groups of the P32a-d polymers include MeO—*,

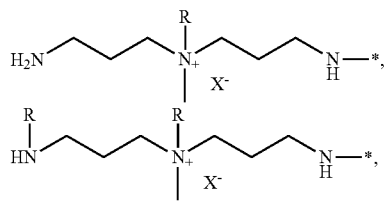

and the like.

Potential Z" end groups of the P32a-d polymers include *—H, the R group of RX,

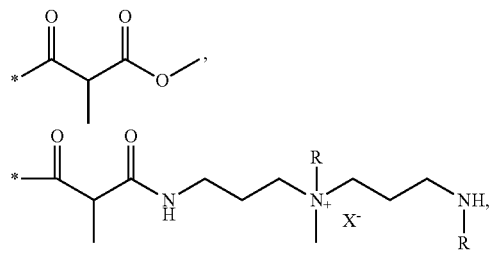

and the like.

Polymers P34a-c were prepared according to the following reaction diagram, where n represents the average number of repeat units enclosed in the parentheses, and n=74.

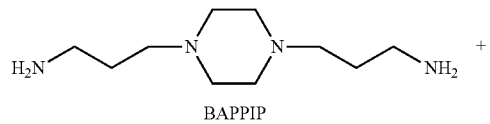

BAPPIP

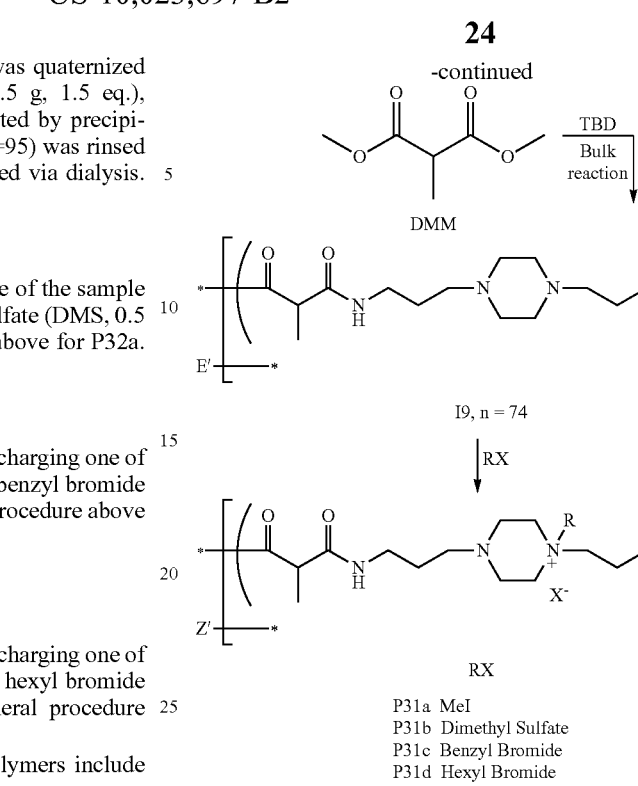

RX
P31a MeI
P31b Dimethyl Sulfate
P31c Benzyl Bromide
P31d Hexyl Bromide

Example 9

Preparation of P34a. 1,4-Bis(3-aminopropyl)piperazine (BAPPIP, 1.57 g, 0.0078 mol), DMM (1.36 g, 0.0078 mol) and TBD (0.05 g, 0.00035 mol) were charged in a Schlenk tube. The reactants were mixed by simple vortex until miscible (1-2 minutes). The reaction was allowed to react at room temperature for 4 hours and then the Schlenk tube was placed in a heated sand bath (80° C., 10 hours). Vacuum was applied to drive off the bi-product and shift the equilibrium towards product. The intermediate polymer I9 crystallized, limiting the molecular weight. Mn (GPC, DMF=20900 g/mol, PDI=1.55, n=74 based on Mn).

Potential E' end groups of I9 include MeO—* and

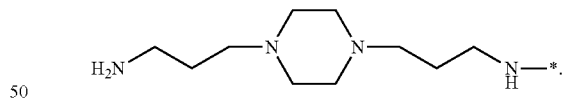

Potential E" end groups of I9 include *—H and

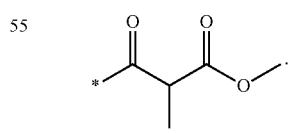

Intermediate polymer I9 was dissolved in DMF (up to 100° C.), and once dissolved was separated into vials (~0.5 g in DMF (8-10 ml)). One of the samples was quaternized (80° C., 24 hours) with methyl iodide (0.5 g, 1.5 eq.), forming P34a. The polymer P34a was isolated by precipitation in diethyl ether. The polymer P34a (n=74) was rinsed 3 times with diethyl ether and further purified via dialysis.

Example 10

P34b (n=74) was prepared by charging one of the sample vials containing polymer I9 with dimethyl sulfate (0.5 g, 1.5 eq.) following the general procedure above for P34a.

Example 11

P34c (n=74) was prepared by prepared by charging one of the sample vials containing polymer I9 with benzyl bromide (0.6 g, 1.5 eq.) following the general procedure above for P34a.

Potential Z' end groups of polymers P34a-c include MeO—*,

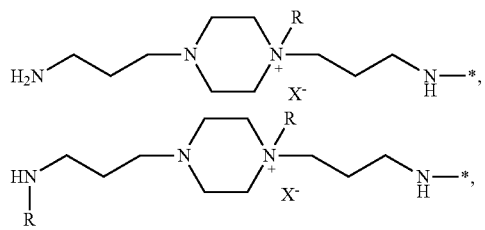

and the like.

Potential Z" end groups of polymers P34a-c include *—H, the R group of RX,

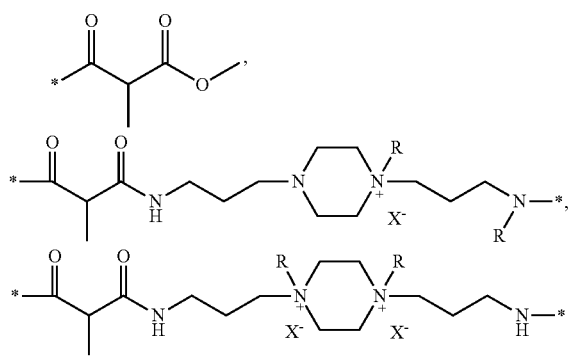

and the like.

Example 12

Preparation of P38 (n=20, RX=methyl iodide).

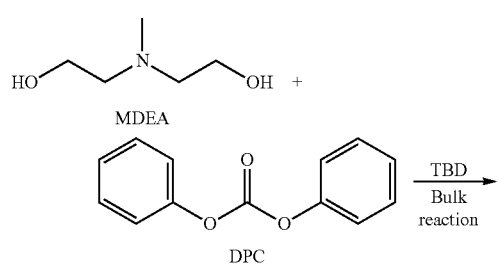

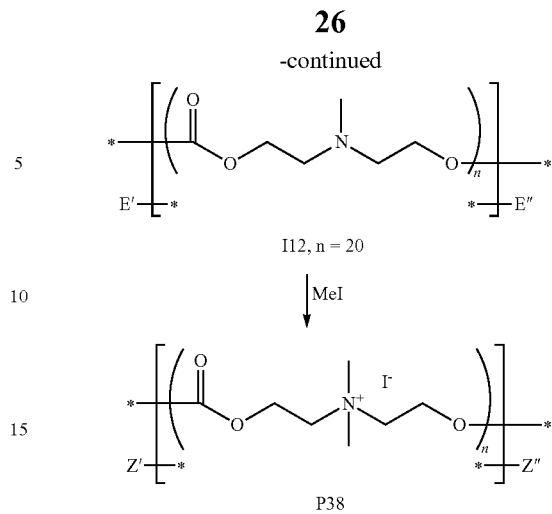

Diphenylcarbonate (DPC, 1.89 g, 0.0088 mol), N-methyldiethanolamine (MDEA, 1.05 g, 0.0088 mol) and TBD (0.05 g, 0.00035 mol) were charged in a Schlenk tube. The reactants were mixed by simple vortex until miscible (1-2 minutes). The Schlenk tube was placed in a heated sand bath (90° C.) and vacuum was applied to pull off the bi-product and shift the equilibrium towards product. The reaction was allowed to continue for 20 hours. The polymerization evolved phenol that eventually sublimed and clogged the valve to the vacuum. The intermediate polymer I12 was dissolved and isolated by filtration to remove the phenol bi-product. Mn (GPC, DMF=3000 g/mol, PDI=1.50, n=20 based on Mn).

Potential E' groups of I12 include PhO—* and

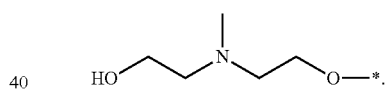

Potential E" groups of I12 include: *—H and

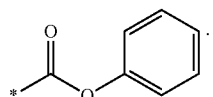

Intermediate polymer I12 was dissolved in DMF and was quaternized (50° C., 24 hours) with methyl iodide. The polymer P38 was rinsed 3 times with diethyl ether and further purified via dialysis.

Potential Z' groups of polymer P38 include PhO—* and

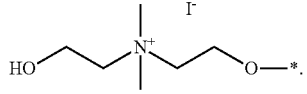

Potential Z" groups of polymer P38 include *—H, methyl and

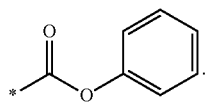

Polymers P48a-b and polymers P49a-b were prepared according to the following reaction diagram, where subscripts u and v represent mol % of the repeating unit enclosed in parentheses, and subscripts r, s, and t, represent average number of repeating units in the brackets. The vertical stacking of the repeat units within the square brackets indicates a random distribution of the repeat units.

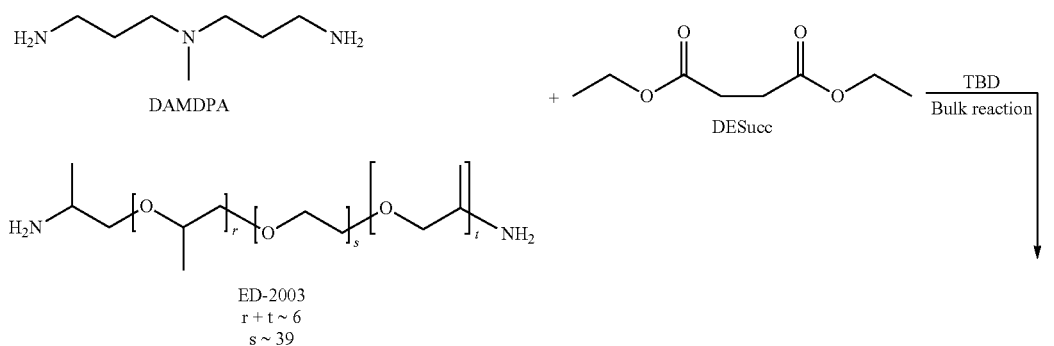

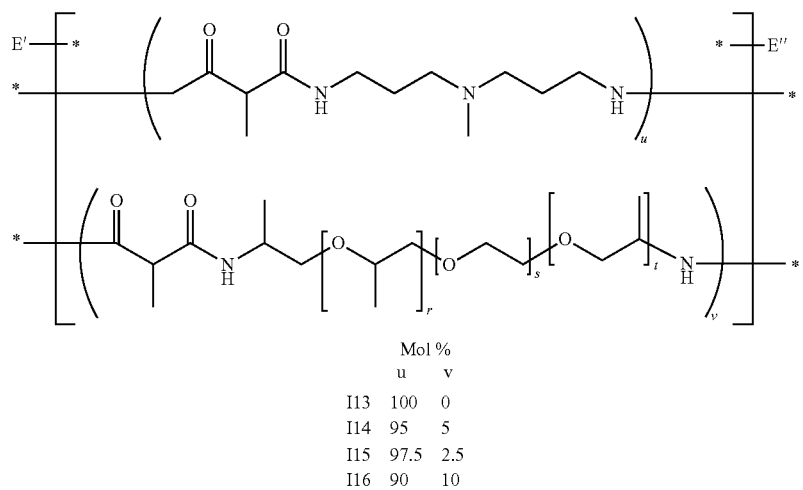

| | Mol % | |
|---|---|---|
| | u | v |
| I13 | 100 | 0 |
| I14 | 95 | 5 |
| I15 | 97.5 | 2.5 |
| I16 | 90 | 10 |

Benzyl Bromide

-continued

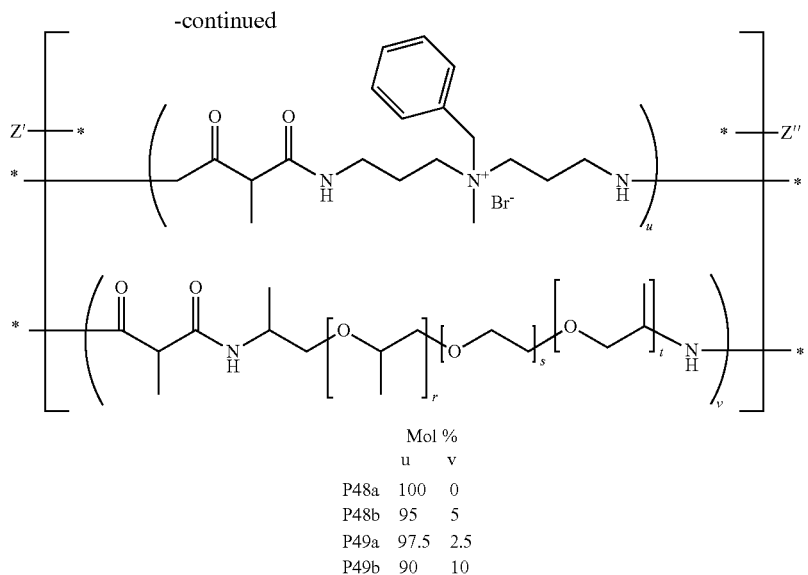

| | Mol % | |
|---|---|---|
| | u | v |
| P48a | 100 | 0 |
| P48b | 95 | 5 |
| P49a | 97.5 | 2.5 |
| P49b | 90 | 10 |

Example 13

Preparation of P48a (u=100 mole %, v=0 mole %, no ED-2003). Diethyl succinate (DESucc, 1.15 g, 0.0063 mol), 3,3'-diamino-N-methyldipropylamine (DAMDPA, 0.92 g, 0.0063 mol) and TBD (0.05 g, 0.00035 mol) were charged in a Schlenk tube. The reactants were mixed by simple vortex until miscible (1-2 minutes). The reaction was allowed to react at room temperature for 4 hours and then the Schlenk tube was placed in a heated sand bath (80° C., 10 hours). Vacuum was applied to drive off the bi-product and shift the equilibrium towards product. The polymer I13 crystallized, limiting the molecular weight.

Potential E' end groups of intermediate polymer I13 include EtO—* and

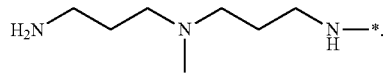

Potential E" end groups of intermediate polymer I13 include *—H and

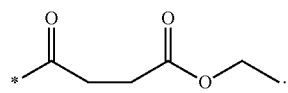 [SMILES: *C(=O)CCC(=O)OCC]

Intermediate polymer I13 was marginally soluble in DMF after heating to 120° C. Once dissolved and homogenous, polymer I13 was quaternized (85° C., 24 hours) with benzyl bromide (2 g, 1.5 eq.). The polymer P48a (u=100 mole %, v=0 mole %) was isolated by precipitation in THF. The polymer was rinsed 3 times with diethyl ether and further purified via dialysis. Mn (aqueous GPC)=4,510 g/mol, PDI=2.19. FIG. 1 is a $^1$H NMR spectrum of P48a.

Potential Z' end groups of P48a include EtO—*,

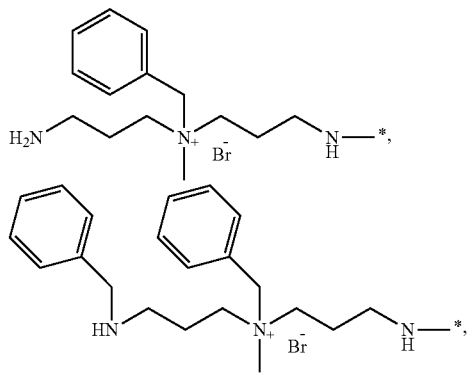

and the like.

Potential Z" end groups of P48a include *—H, benzyl,

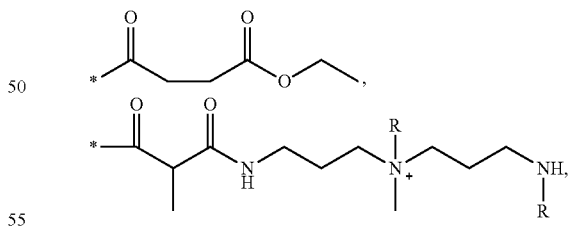

and the like.

Example 14

Preparation of P48b (u=95 mole %, v=5 mole %) using 5 mol % ED-2003. Diethyl succinate (DESucc, 1.02 g, 0.0058 mol), 3,3'-diamino-N-methyldipropylamine (DAMDPA, 0.83 g, 0.0055 mol), ED-2003 (0.58 g, 0.00029 mol, s~39, r+t~6) and TBD (0.05 g, 0.00035 mol) were charged in a Schlenk tube. The reactants were mixed by simple vortex until miscible (1-2 minutes). The reaction was allowed to react at room temperature for 4 hours and then the Schlenk tube was placed in a heated sand bath (80° C., 10 hours). Vacuum was applied to drive off the bi-product and shift the equilibrium towards product. The polymer I14 crystallized, limiting the molecular weight.

Potential E' end groups of intermediate polymer I14 include those mentioned above for polymer I13, and

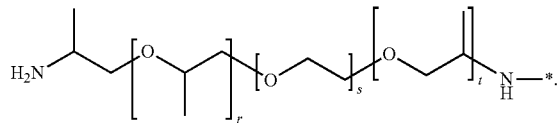

Potential E" end groups of intermediate polymer I14 include those mentioned above for polymer I13.

Figure 2:
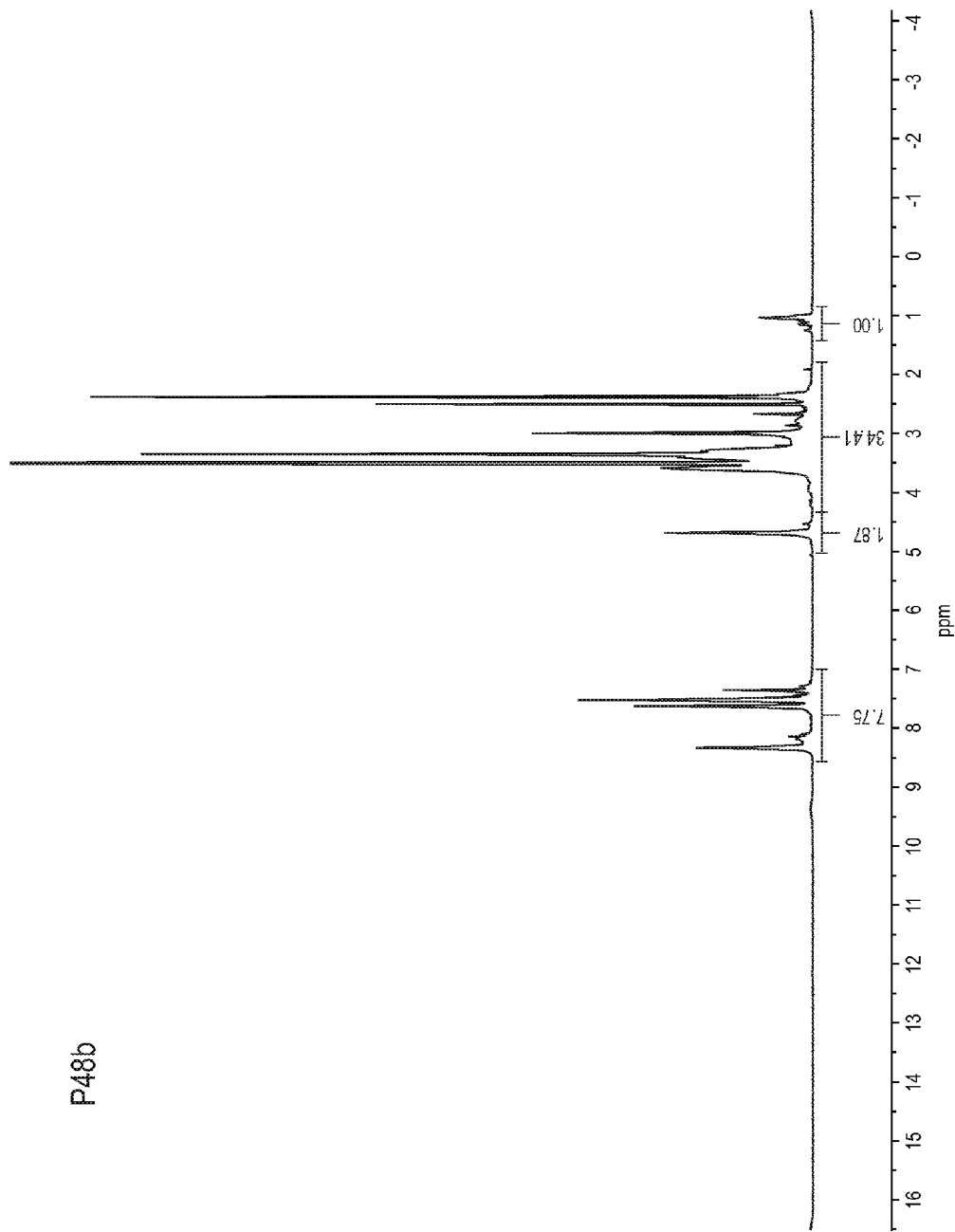
FIG. 2 is a $^1$H NMR spectrum of cationic polymer P48b.

Intermediate polymer I14 was marginally soluble in DMF after heating to 120° C. for 2-3 hours. Once dissolved and homogenous, the polymer was quaternized (85° C., 24 hours) with benzyl bromide (2.8 g, 1.5 eq.). The polymer P48b was isolated by precipitation in THF. The polymer P48b (u=95 mole %, v=5 mole %) was rinsed 3 times with diethyl ether and further purified via dialysis. Mn (Aqueous GPC)=1,960 g/mol, PDI=1.66. FIG. 2 is a $^1$H NMR spectrum of P48b.

Potential Z' end groups of the P48b polymer include those mentioned above for P48a, and also

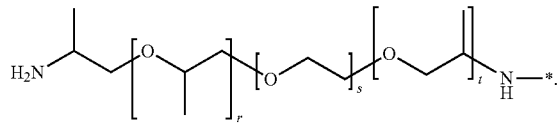

Potential Z" end groups of polymer P48b include those mentioned above for polymer P48a.

Example 15

Preparation of P49a (u=97.5 mole %, v=2.5 mole %) using 2.5 mol % ED-2003. Diethyl succinate (DESucc, 1.14 g, 0.0066 mol), 3,3'-diamino-N-methyldipropylamine (DAMDPA, 0.93 g, 0.0064 mol), ED-2003 (0.26 g, 0.00013 mol) and TBD (0.05 g, 0.00035 mol) were charged in a Schlenk tube. The reactants were mixed by simple vortex until miscible (1-2 minutes). The reaction was allowed to react at room temperature for 4 hours and then the Schlenk tube was placed in a heated sand bath (80° C., 10 hours). Vacuum was applied to drive off the bi-product and shift the equilibrium towards product. The polymer I15 crystallized, limiting the molecular weight.

Potential E' and E" end groups include those mentioned above for 114.

Figure 3:
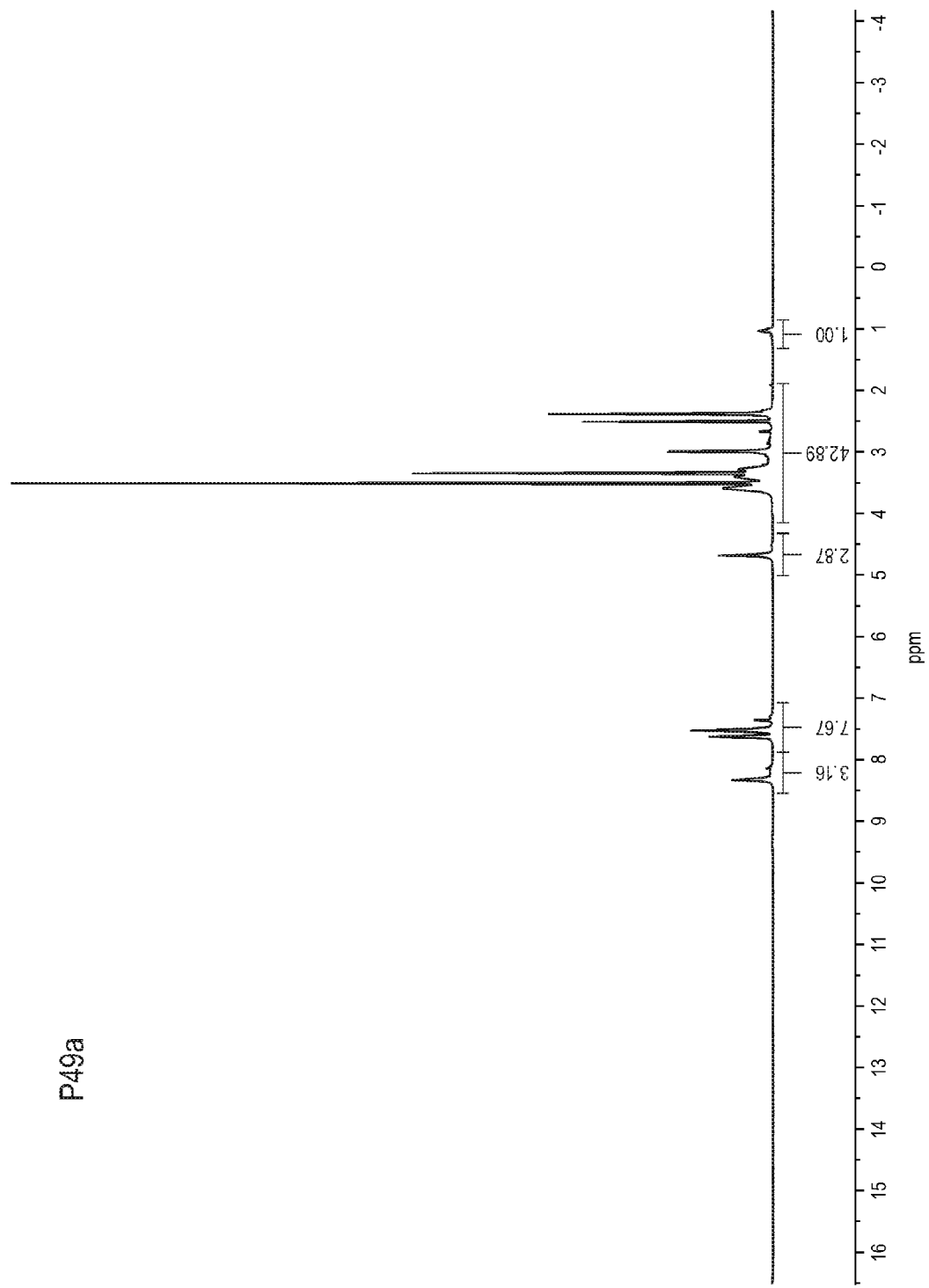

Intermediate polymer I15 was marginally soluble in DMF after heating to 120° C. for 2-3 hours. Once dissolved and homogenous, the polymer was quaternized (85° C., 24 hours) with benzyl bromide (2.5 g, 1.5 eq.). The polymer P49a was isolated by precipitation in THF. The polymer P49a (u=97.5 mole %, v=2.5 mole %) was rinsed 3 times with diethyl ether and further purified via dialysis. Mn (Aqueous GPC)=2,100 g/mol, PDI=1.75. FIG. 3 is a $^1$H NMR spectrum of P49a.

Potential Z' and Z" end groups of P49a include those mentioned above for P48b.

Example 16

Preparation of P49b (u=97.5 mole %, v=2.5 mole %) using 10.0 mol % ED-2003. Diethyl succinate (1.25 g, 0.0072 mol), 3,3'-diamino-N-methyldipropylamine (0.94 g, 0.0064 mol), ED-2003 (1.44 g, 0.00072 mol) and TBD (0.05 g, 0.00035 mol) were charged in a Schlenk tube. The reactants were mixed by simple vortex until miscible (1-2 minutes). The reaction was allowed to react at room temperature for 4 hours and then the Schlenk tube was placed in a heated sand bath (80° C., 10 hours). Vacuum was applied to drive off the bi-product and shift the equilibrium towards product. The polymer I16 crystallized, limiting the molecular weight.

Potential E' and E" end groups of I16 include those mentioned above for P14.

Figure 4:
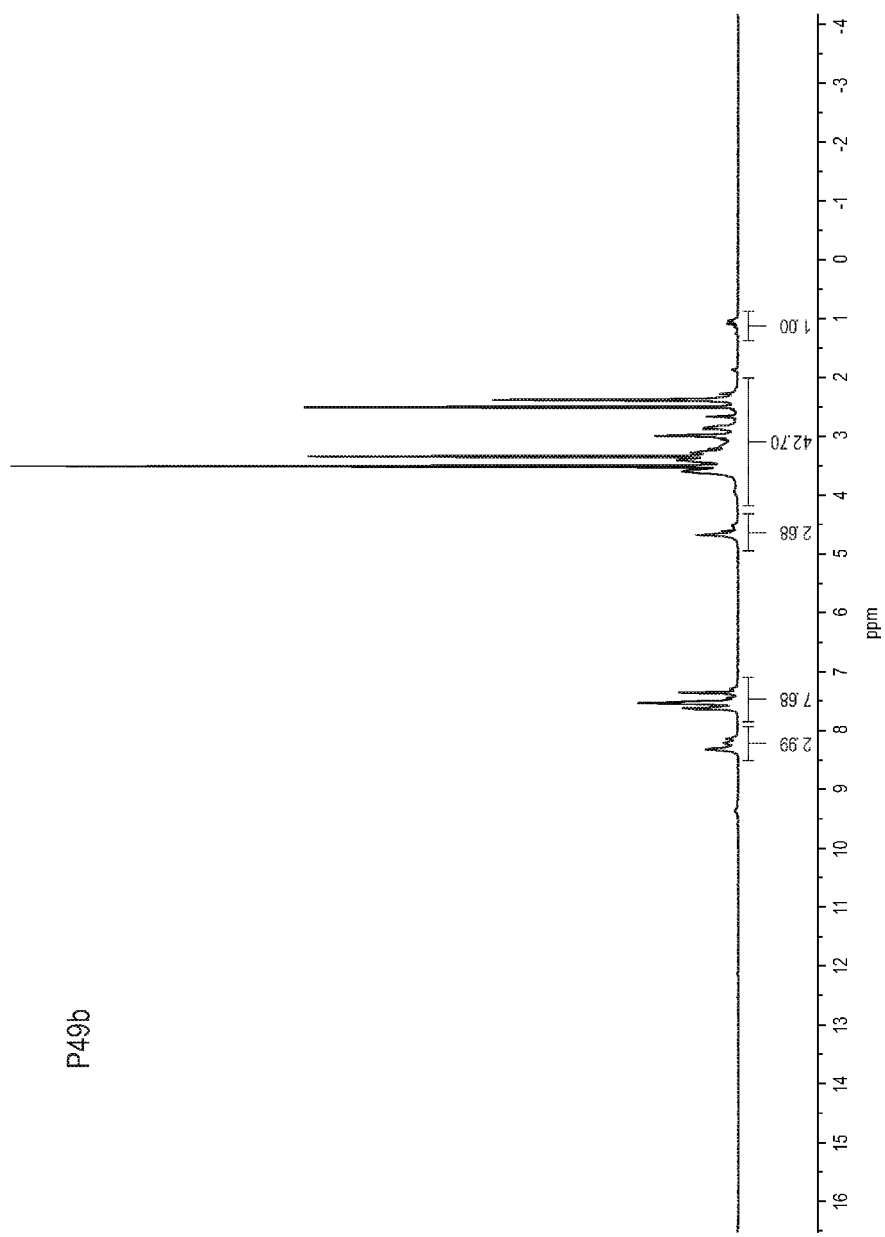
FIG. 4 is a $^1$H NMR spectrum of cationic polymer P49b.

Intermediate polymer I16 was marginally soluble in DMF after heating to 120° C. for 2-3 hours. Once dissolved and homogenous, the polymer I16 was quaternized (85° C., 24 hours) with benzyl bromide (2.2 g, 1.5 eq.). The polymer P49b was isolated by precipitation in THF. The polymer P49b (u=97.5 mole %, v=2.5 mole %) was rinsed 3 times with diethyl ether and further purified via dialysis. Mn (Aqueous GPC)=2,800 g/mol, PDI=1.69. FIG. 4 is a $^1$H NMR spectrum of P49b.

Potential Z' and Z" end groups of P49b include those mentioned above for P48b.

Polymers P59a-f were prepared according to the following reaction diagram, where subscripts u and v represent mole percentages. Subscripts r, s, and t represent average degree of polymerization.

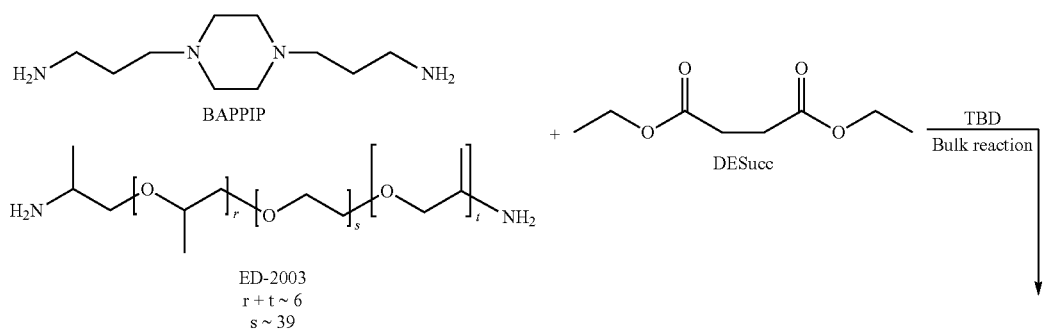

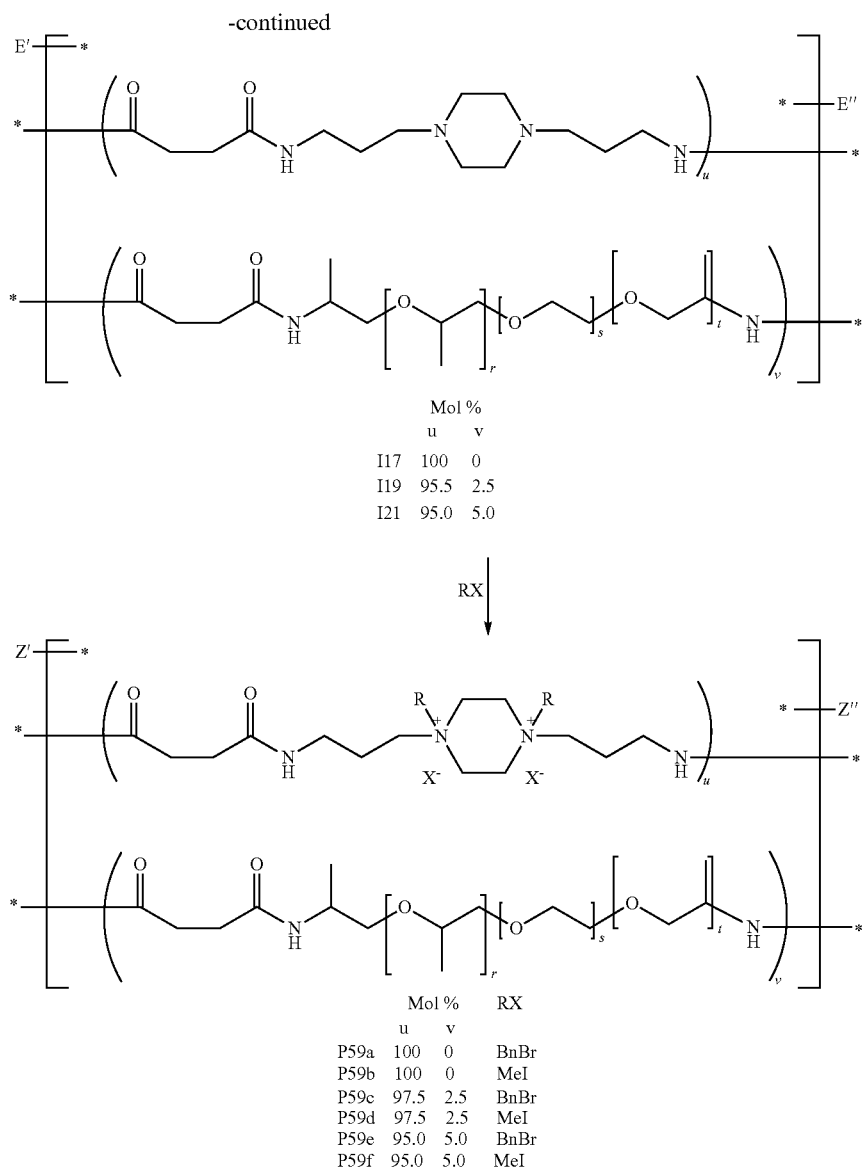

Example 17

Preparation of P59a (u=100 mole %, v=0 mole %, r>0, t>0, r+t~6, s~39, DP=19, RX=benzyl bromide) using 0 mol % ED-2003. Diethyl succinate (DESucc, 1.40 g, 0.0080 mol), 3,3'-bis(3-aminopropyl)piperazine (BAPPIP, 1.61 g, 0.0080 mol), and TBD (0.05 g, 0.00035 mol) were charged in a Schlenk tube. The reactants were mixed by simple vortex until miscible (1-2 minutes). The reaction was allowed to react at room temperature for 4 hours and then the Schlenk tube was placed in a heated sand bath (100° C., 1.5 hours) followed by heating at 150° C., 24 hours. Vacuum was applied to remove the alcohol byproduct and shift the equilibrium towards product. The polymer I17 crystallized, limiting the molecular weight. Mn (GPC, DMF=5500 g/mol, PDI=1.20, u=100 mol %, v=0 mol %, degree of polymerization (DP)=19).

Intermediate polymer I18 was marginally soluble in DMF after heating to 120° C. Once dissolved and homogenous, the polymer I17 was quaternized (85° C., 24 hours) with benzyl bromide (5 g, 3 eq.) Polymer P59a (u=100 mole %, v=0 mole %, r>0, t>0, r+t~6, s~39, RX=benzyl bromide) was isolated by precipitation in THF. The polymer P59a was rinsed 3 times with diethyl ether and further purified via dialysis.

Example 18

Preparation of P59b (u=100 mole %, v=0 mole %, r>0, t>0, r+t~6, s~39, DP=19, RX=methyl iodide) with 0 mol % ED-2003. Intermediate polymer I17 was quaternized with MeI (4 g, 3 eq.) using the general procedure described above for P59a.

Example 19

Preparation of P59c (u=97.5 mole %, v=2.5 mole %, r>0, t>0, r+t~6, s~39, RX=benzyl bromide) with 2.5 mol % ED-2003. Diethyl succinate (DESucc, 1.29 g, 0.0074 mol), ED-2003 (0.37 g, 0.00018 mol) and TBD (0.05 g, 0.00035 mol) were charged in a Schlenk tube. The reactants were mixed by simple vortex until miscible (1-2 minutes). The reaction was allowed to react under nitrogen for 1 hour (100° C.). 3,3'-Bis(3-aminopropyl)piperazine (1.45 g, 0.0082 mol) was charged in the Schlenk tube was placed in a heated sand bath (150° C., 20 hours). Vacuum was applied to drive off the bi-product and shift the equilibrium towards product. The intermediate polymer I19 crystallized, limiting the molecular weight. Mn (GPC, DMF=7500 g/mol, PDI=1.20; u=97.5 mol %, v=2.5 mol % based on feed).

Intermediate polymer I19 was marginally soluble in DMF after heating to 120° C. (2-3 hours). Once dissolved and homogenous, I19 was quaternized (85° C., 24 hours) with benzyl bromide (6 g, 3 eq.) The product polymer P59c (u=97.5 mole %, v=2.5 mole %, r>0, t>0, r+t~6, s~39, RX=benzyl bromide) was isolated by precipitation in THF. The polymer P59c was rinsed 3 times with diethyl ether and further purified via dialysis.

Example 20

Preparation of P59d (u=97.5 mole %, v=2.5 mole %, r>0, t>0, r+t~6, s~39, RX=methyl iodide) with 2.5 mol % ED-2003. Intermediate polymer I19 was quaternized with MeI (5.6 g, 3 eq.) using the general procedure described above to yield P59d.

Example 21

Preparation of P59e (u=95.0 mole %, v=5.0 mole %, r>0, t>0, r+t~6, s~39, RX=benzyl bromide) with 5 mol % ED-2003. Diethyl succinate (DESucc, 1.05 g, 0.0058 mol), ED-2003 (0.58 g, 0.00029 mol) and TBD (0.05 g, 0.00035 mol) were charged in a Schlenk tube. The reactants were mixed by simple vortex until miscible (1-2 minutes). The reaction was allowed to react under nitrogen for 1 hour (100° C.). 3,3'-Bis(3-aminopropyl)piperazine (1.10 g, 0.0055 mol) was added to the Schlenk tube, and the Schlenk tube was placed in a heated sand bath (150° C., 20 hours). Vacuum was applied to drive off the bi-product and shift the equilibrium towards product. The polymer I21 crystallized, limiting the molecular weight.

Intermediate polymer I21 was marginally soluble in DMF after heating to 120° C. (2-3 hours). Once dissolved and homogenous, I21 was quaternized (85° C., 24 hours) with benzyl bromide (2.6 g, 3 eq.). The polymer P59e (u=95.0 mole %, v=5.0 mole %, r>0, t>0, r+t~6, s~39, RX=benzyl bromide) was isolated by precipitation in THF. The polymer P59e was rinsed 3 times with diethyl ether and further purified via dialysis.

Example 22

Preparation of P59f (u=95.0 mole %, v=5.0 mole %, r>0, t>0, r+t~6, s~39, RX=methyl iodide) with 5 mol % ED-2003. Intermediate polymer I21 was quaternized with MeI (2.3 g, 3 eq.) using the general procedure described above to form P59f.

The P60 series of polymers was made according to the following reaction diagram, where subscripts u and v represent mole percentages and subscripts r, s, and t represent average degree of polymerization.

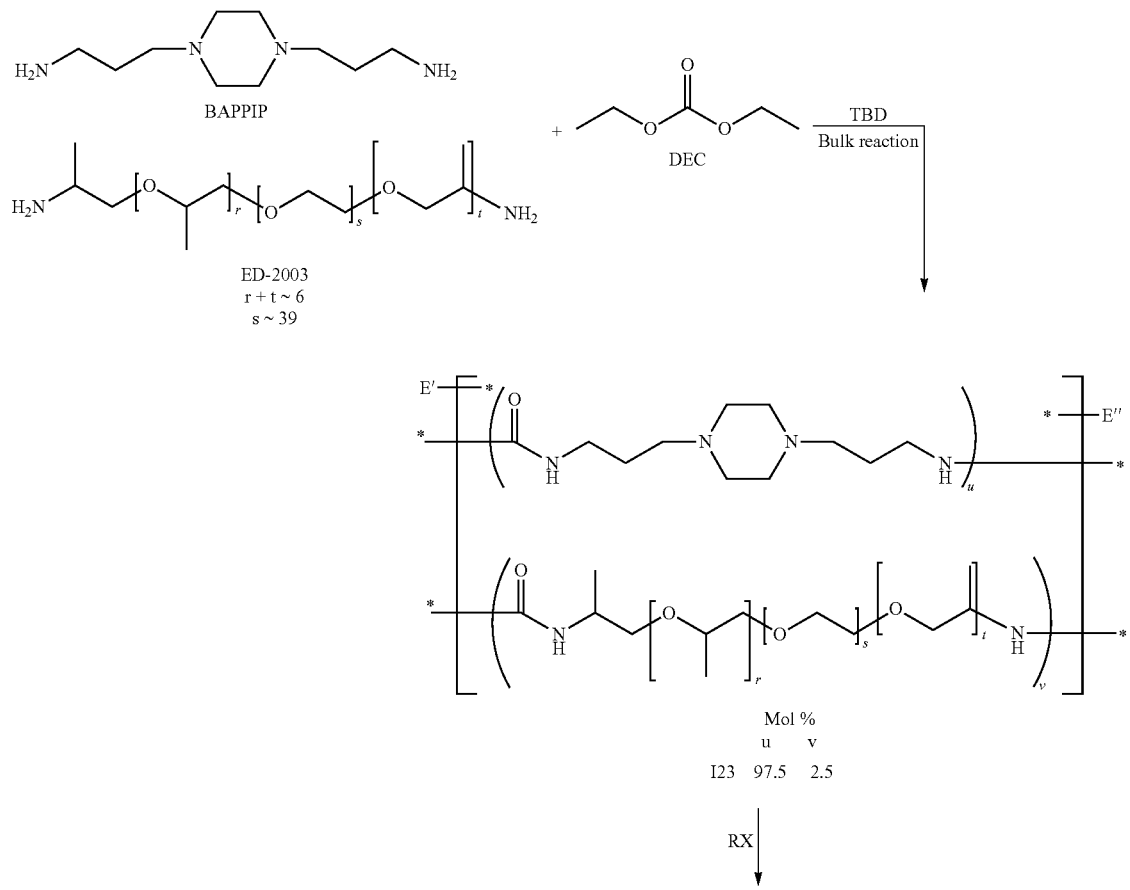

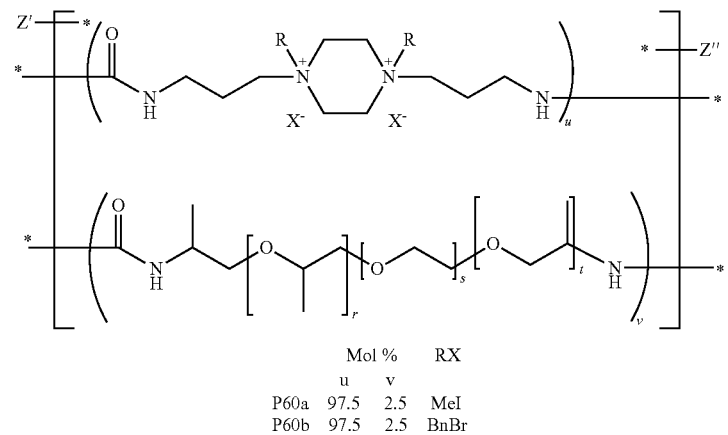

| | Mol % | | RX |
|---|---|---|---|
| | u | v | |
| P60a | 97.5 | 2.5 | MeI |
| P60b | 97.5 | 2.5 | BnBr |

Example 23

Preparation of P60a (u=97.5 mole %, v=2.5 mole %, r>0, t>0, r+t~6, s~39, RX=methyl iodide) with 2.5 mol % ED-2003. Diethyl carbonate (DEC, 1.09 g, 0.0089 mol), ED-2003 (0.46 g, 0.00023 mol) and TBD (0.05 g, 0.00035 mol) were combined in a Schlenk tube. The reactants were mixed by simple vortex until miscible (1-2 minutes). The reaction was allowed to react under nitrogen for 1 hour (100° C.). 3,3'-Bis(3-aminopropyl)piperazine (1.45 g, 0.0082 mol) was added to the Schlenk tube, and the Schlenk tube was placed in a heated sand bath (150° C., 20 hours). Vacuum was applied to drive off the bi-product and shift the equilibrium towards product. The intermediate polymer I24 crystallized, limiting the molecular weight. Mn (GPC, DMF=8500 g/mol, PDI=broad and multimodal; u=97.5 mol %, v=2.5 mol % based on feed).

Intermediate polymer I23 was marginally soluble in DMF after heating to 120° C. (2-3 hours). Once dissolved and homogenous, the polymer I24 was quaternized (85° C., 24 hours) with methyl iodide (~3 g, 2.5-3 eq.). The product polymer P60a was isolated by precipitation in THF. The polymer P60a (u=97.5 mole %, v=2.5 mole %, r>0, t>0, r+t~6, s~39, RX=methyl iodide) was rinsed 3 times with diethyl ether and further purified via dialysis.

Example 24

Preparation of P60b with 2.5 mol % ED-2003. Intermediate polymer I23 was quaternized with benzyl bromide using the general procedure described above for P60a (u=97.5 mole %, v=2.5 mole %, r>0, t>0, r+t~6, s~39, RX=benzyl bromide).

Polymers P73a-d were made according to the following reaction diagram, where subscripts u and v represent mole percentages and subscripts r, s, and t represent average degree of polymerization.

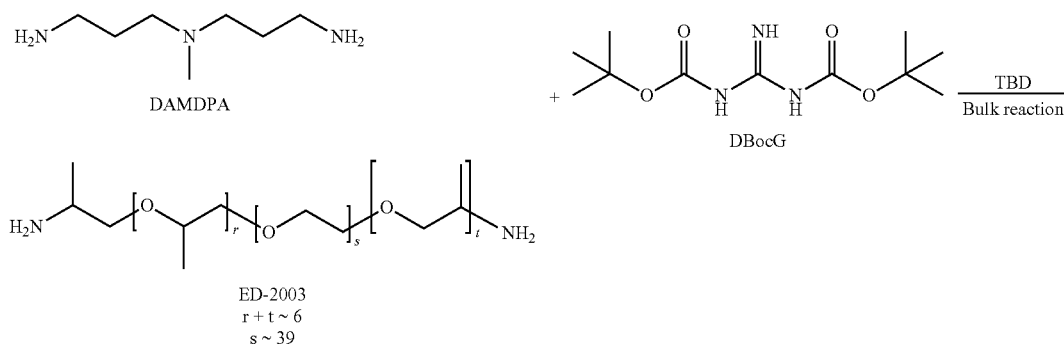

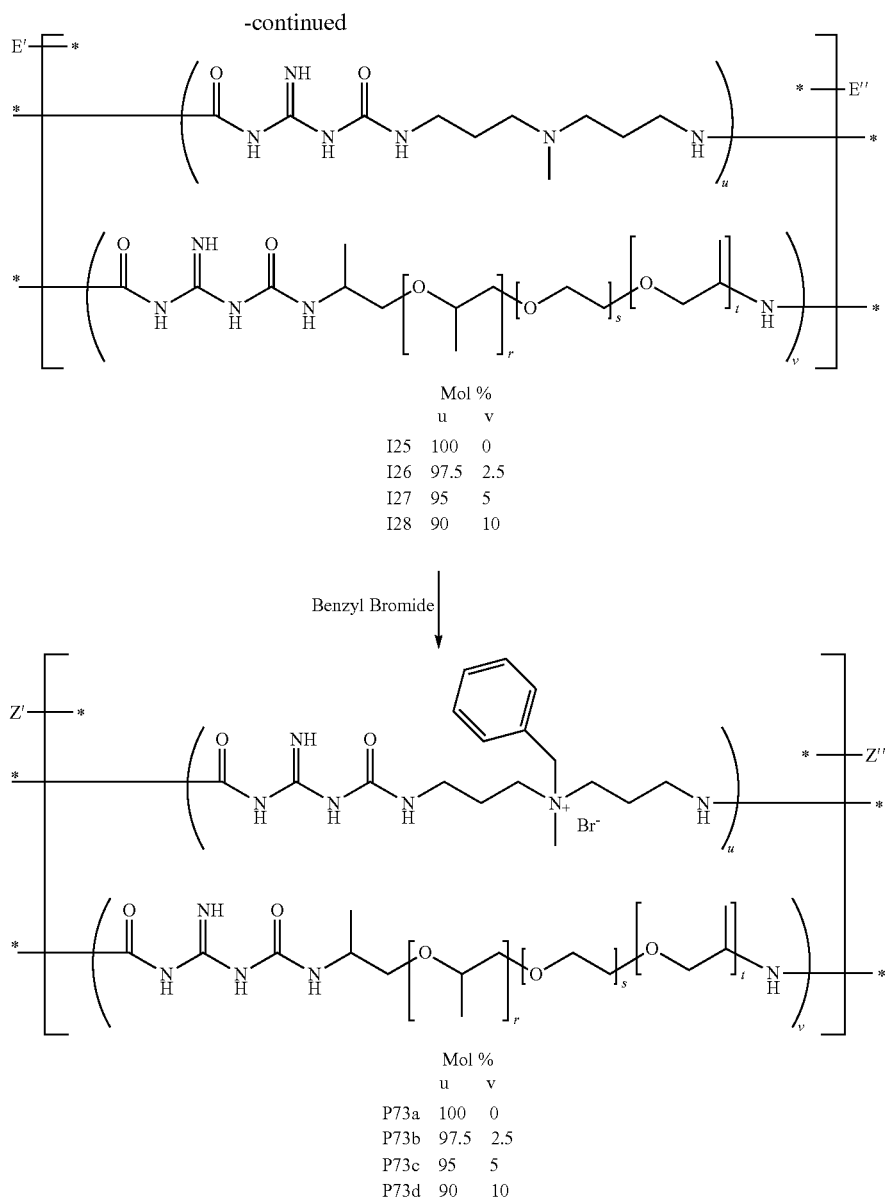

Example 25

Preparation of P73a (u=100 mole %, v=0 mole %, r>0, t>0, r+t~6, s~39, RX=benzyl bromide) with 0 mol % ED-2003. Di-boc-guanidine (DBocG, 1.00 g, 0.0038 mol), 3,3'-diamino-N-methyldipropylamine (DAMDPA, 0.92 g, 0.0038 mol) and TBD (0.05 g, 0.00035 mol) were combined in a Schlenk tube. The reactants were mixed by simple vortex until miscible (1-2 minutes). The reaction was allowed to react at room temperature for 4 hours and then the Schlenk tube was placed in a heated sand bath (150° C., 10 hours). Vacuum was pulled to drive off the bi-product and shift the equilibrium towards product. The intermediate polymer I25 solidified as a rigid, solvent swollen gel, limiting the molecular weight.

Intermediate polymer I25 was soluble in DMF at room temperature. Once dissolved and homogenous, I26 was quaternized (25° C., 24 hours) with benzyl bromide (0.7 g, 1.0 eq.). The polymer P73a (u=100 mole %, v=0 mole %, r>0, t>0, r+t~6, s~39, RX=benzyl bromide) was isolated by precipitation in diethyl ether. The polymer P73a was rinsed 3 times with diethyl ether and further purified via dialysis.

Example 26

Preparation of P73b (u=97.5 mole %, v=2.5 mole %, r>0, t>0, r+t~6, s~39, RX=benzyl bromide) with 2.5 mol % ED-2003. Di-boc-guanidine (DBocG, 1.00 g, 0.0038 mol), 3,3'-diamino-N-methyldipropylamine (DAMDPA, 0.547 g, 0.00376 mol), ED-2003 (0.193 g, 0.000096 mol) and TBD (0.05 g, 0.00035 mol) were charged in a Schlenk tube. The reactants were mixed by simple vortex until miscible (1-2 minutes). The reaction was allowed to react at room temperature for 4 hours and then the Schlenk tube was placed in a heated sand bath (150° C., 20 hours). Vacuum was applied to drive off the bi-product and shift the equilibrium towards product. The polymer I26 solidified as a rigid, solvent swollen gel. The polymerization becomes diffusion controlled, limiting the molecular weight.

Intermediate polymer I26 was marginally soluble in DMF after heating to 100° C. (30 minutes). Once dissolved and homogenous, I26 was quaternized (25° C., 24 hours) with benzyl bromide (0.6 g, 1.0 eq.). As the reaction proceeded it progressively became more homogeneous until solvated. The polymer P73b (u=97.5 mole %, v=2.5 mole %, r>0, t>0, r+t~6, s~39, RX=benzyl bromide) was isolated by precipitation in THF. The polymer P73b was rinsed 3 times with diethyl ether and further purified via dialysis.

Example 27

Preparation of P73c (u=95.0 mole %, v=5.0 mole %, r>0, t>0, r+t~6, s~39, RX=benzyl bromide) with 5.0 mol % ED-2003. Di-boc-guanidine (1.00 g, 0.0038 mol), 3,3'-diamino-N-methyldipropylamine (DAMDPA, 0.53 g, 0.00366 mol), ED-2003 (0.386 g, 0.000192 mol) and TBD (0.05 g, 0.00035 mol) were charged in a Schlenk tube. The reactants were mixed by simple vortex until miscible (1-2 minutes). The reaction was allowed to react at room temperature for 4 hours and then the Schlenk tube was placed in a heated sand bath (150° C., 20 hours). Vacuum was applied to drive off the bi-product and shift the equilibrium towards product. The polymer I27 solidified as a rigid, solvent swollen gel. The polymerization becomes diffusion controlled, limiting the molecular weight.

Example 28

Preparation of P73d (u=90.0 mole %, v=10.0 mole %, r>0, t>0, r+t~6, s~39, RX=benzyl bromide) with 10.0 mol % ED-2003. Di-boc-guanidine (DBocG, 1.00 g, 0.0038 mol), 3,3'-diamino-N-methyldipropylamine (DAMDPA, 0.50 g, 0.0034 mol), ED-2003 (0.772 g, 0.00038 mol), and TBD (0.05 g, 0.00035 mol) were charged in a Schlenk tube. The reactants were mixed by simple vortex until miscible (1-2 minutes). The reaction was allowed to react at room temperature for 4 hours and then the Schlenk tube was placed in a heated sand bath (150° C., 20 hours). Vacuum was applied to drive off the bi-product and shift the equilibrium towards product. The polymer I28 solidified as a rigid, solvent swollen gel. The polymerization becomes diffusion controlled, limiting the molecular weight.

Intermediate polymer I28 was marginally soluble in DMF after heating to 100° C. (30 minutes). Once dissolved and homogenous, the polymer I28 was quaternized (25° C., 24 hours) with benzyl bromide. As the reaction proceeded it progressively became more homogeneous until solvated (0.6 g, 1 eq.). The polymer P73d (u=95.0 mole %, v=5.0 mole %, r>0, t>0, r+t~6, s~39, RX=benzyl bromide) was isolated by precipitation in THF. The polymer P73d was rinsed 3 times with diethyl ether and further purified via dialysis.

Table 2 summarizes the polymers formed.

TABLE 2

| Example | Polymer Name | Carbonyl Monomer | Amine Monomer | Amine Monomer (mol %) | ED-2003 (mol %) | RX | Mn | PDI |
|---|---|---|---|---|---|---|---|---|
| 1 | P31a | DMM | MDEA | 100 | 0 | MeI | | |
| 2 | P31b | DMM | MDEA | 100 | 0 | DMS | | |
| 3 | P31c | DMM | MDEA | 100 | 0 | BnBr | | |
| 4 | P31d | DMM | MDEA | 100 | 0 | HexBr | | |
| 5 | P32a | DMM | DAMDPA | 100 | 0 | MeI | | |
| 6 | P32b | DMM | DAMDPA | 100 | 0 | DMS | | |
| 7 | P32c | DMM | DAMDPA | 100 | 0 | BnBr | | |
| 8 | P32d | DMM | DAMDPA | 100 | 0 | HexBr | 1,020 | 1.19 |
| 9 | P34a | DMM | BAPPIP | 100 | 0 | MeI | | |
| 10 | P34b | DMM | BAPPIP | 100 | 0 | DMS | | |
| 11 | P34c | DMM | BAPPIP | 100 | 0 | BnBr | | |
| 12 | P38 | DPC | MDEA | 100 | 0 | MeI | | |
| 13 | P48a | DESucc | DAMDPA | 100 | 0 | BnBr | 4,510 | 2.19 |
| 14 | P48b | DESucc | DAMDPA | 95 | 5 | BnBr | 4,670 | 1.94 |
| 15 | P49a | DESucc | DAMDPA | 97.5 | 2.5 | BnBr | 3,100 | 1.77 |
| 16 | P49b | DESucc | DAMDPA | 90 | 10 | BnBr | 2,270 | 1.88 |
| 17 | P59a | DESucc | BAPPIP | 100 | 0 | BnBr | 1,740 | 1.89 |
| 18 | P59b | DESucc | BAPPIP | 100 | 0 | MeI | 2,860 | 1.92 |
| 19 | P59c | DESucc | BAPPIP | 97.5 | 2.5 | BnBr | 3,510 | 1.89 |
| 20 | P59d | DESucc | BAPPIP | 97.5 | 2.5 | MeI | 3,000 | 1.67 |
| 21 | P59e | DESucc | BAPPIP | 95 | 5.0 | BnBr | | |
| 22 | P59f | DESucc | BAPPIP | 95 | 5.0 | MeI | | |
| 23 | P60a | DEC | BAPPIP | 97.5 | 2.5 | MeI | | |
| 24 | P60b | DEC | BAPPIP | 97.5 | 2.5 | BnBr | | |
| 25 | P73a | DBocG | DAMDPA | 100 | 0 | BnBr | | |
| 26 | P73b | DBocG | DAMDPA | 97.5 | 2.5 | BnBr | | |
| 27 | P73c | DBocG | DAMDPA | 95 | 5 | BnBr | | |
| 28 | P73d | DBocG | DAMDPA | 90 | 10 | BnBr | | |

Minimum inhibitory concentration (MIC)

Intermediate polymer I27 was marginally soluble in DMF after heating to 100° C. (30 minutes). Once dissolved and homogenous, I27 was quaternized (25° C., 24 hours) with benzyl bromide (0.6 g, 1 eq.). As the reaction proceeded it progressively became more homogeneous until solvated. The polymer P73c (u=95.0 mole %, v=5.0 mole %, r>0, t>0, r+t~6, s~39, RX=benzyl bromide) was isolated by precipitation in THF. The polymer P73c was rinsed 3 times with diethyl ether and further purified via dialysis.

Bacterial samples were inoculated in TSB (or MHB) at 37° C., whereas fungi samples were inoculated in YMB (or MHB) at room temperature, both under constant shaking of 100 rpm (revolutions per minute). The samples were grown overnight to enter the log growth phase. A broth microdilution method was used to determine the respective MIC of each polymer, where 100 microliters of broth containing a polymer with a constant de-ionized (DI) water content of 20% v/v at various concentrations was placed in each well of a 96-well culture plate. Prior to the addition of an equal volume of microbial solution into each well, the concentration of the microbial solution was first adjusted to obtain an optical density (O.D.) reading of approximately 0.07 at 600 nm using a microplate reader (TECAN, Switzerland), which corresponds to the concentration of McFarland 1 solution of $3\times10^8$ colony forming units (CFU)/mL and followed by a 1000-time dilution to achieve an initial loading of $3\times10^5$ CFU/mL. The 96-well plate was then incubated at 37° C. for bacterial samples and room temperature for fungi samples under constant shaking of 100 rpm for 18 hours and 42 hours, respectively. MIC was regarded to be the least concentration where no observable microbial growth was detected by the microplate reader after the incubation duration. Broth containing only microbes was used as the negative control. Six replicates were tested for each concentration of polymer and the control.

Killing Efficiency Test

The same procedure as described for MIC measurement was used to determine the concentration of polymer that kills the microbes, and the microbial samples were inoculated and prepared accordingly. After incubating for 18 hours for bacterial samples and 42 hours for fungi samples, wells containing polymers at various concentrations of 0.0MIC (0.0 times MIC), 0.5MIC (0.5×MIC), 1.0MIC (1.0×MIC), and 2.0MIC (2.0×MIC) were collected individually and diluted through a series of tenfold. The diluted microbial solution (20 microliters) was streaked onto an agar plate (LB Agar from 1st Base). The plates were then incubated for 18 hours at 37° C. for bacterial samples and 42 hours at room temperature for fungi samples. The colony-forming units on each plate were counted.

Killing Kinetics Test

The same procedure as described for the killing efficiency test was used to assess the duration time required for polymers to achieve 99.9 killing efficiency of microbes. Eight duration times of 0, 0.25, 0.5, 1, 2, 4, 8 and 18 hours were selected, and the microbes were treated at 1.0MIC and 2.0MIC concentration of polymers.

For polymers P31a, P31c, P31a, P32a, P32b, P32d, P34a, P34b, P48a, P48b, P49a and P49b, TSB was used for all bacterial samples and YMB for fungi samples when assessing antimicrobial activities.

Hemolysis Assay

Fresh rat red blood cells (RBCs) suspension was diluted 25 times with PBS to achieve 4% v/v blood content. Polymers were dissolved in PBS at various concentrations with a constant DI water concentration of 20% v/v. Diluted blood suspension was treated with an equal volume of polymer solution and incubated at 37° C. for 1 hour. After centrifugation of the mixtures at 1000 g-force for 5 minutes at 4° C., 100 microliters of supernatant was transferred into a 96-well culture plate, with 4 replicates for each polymer concentration. The hemoglobin released was then measured using a microplate reader (TECAN, Switzerland) at 576 nm. Untreated RBCs suspension was used as the negative control while RBCs suspension treated with 0.1% Triton-X was the positive control. Percentage of hemolysis was calculated as follows:

Hemolysis (%)=[(O.D.$_{576\ nm}$ of the treated sample–O.D.$_{576\ nm}$ of negative control)/(O.D.$_{576\ nm}$ of positive control–O.D.$_{576\ nm}$ of negative control)]×100%

In Vitro Cytotoxicity

Cytotoxicity of polymers was investigated by MTT assay, where HDF cells were seeded on 96-well plates at a density of $10^4$ cells per well, and cultured in 100 microliters of DMEM supplemented with 10% FBS, 5% penicillin-streptomycin, 2 mM L-glutamine, 4.5 g/L D-glucose and 110 mg/L sodium pyruvate, and incubated at 37° C., 5% $CO_2$ for 24 hours. Polymers were dissolved in the cell culture medium at various concentrations. The prepared solution (100 microliters) was then used to substitute the medium in each well. Each condition was tested in six replicates. The plates were then incubated at 37° C., 5% $CO_2$ for 6 hours. After 6 hours of treatment with the polymer, 100 microliters of fresh culture medium and 20 microliters of MTT solution (5 mg/mL) were added to replace the solution in each well. The plates were then maintained at 37° C., 5% $CO_2$ for 4 hours. Dimethyl sulfoxide (150 microliters) was added to each well to dissolve the internalized purple formazan crystals after removing the medium. The absorbance readings of formazan crystals were taken to be the absorbance at 550 nm subtracted by the absorbance at 690 nm (TECAN, Switzerland). Cell viability was expressed as a percentage of absorbance of the control cells without any treatment.

Antimicrobial Activity

Antimicrobial activity of the polymers was assessed against four different microbes of clinical relevance: *Staphylococcus aureus, Escherichia coli, Pseudomonas aeruginosa*, and *Candida albicans*. The minimum inhibitory concentrations (MICs) of all polymers were determined using the broth microdilution method, and were taken to be the lowest concentration where no observable microbial growth was detected by the microplate reader after the incubation duration with an initial microbial loading of $3\times10^5$ CFU/mL. Toxicity of polymers was evaluated via the hemolysis assay with fresh rat red blood cells. Both MIC and 50% hemolysis ($HC_{50}$) values of the respective polymers are listed in Table 3. Lower MIC and higher $HC_{50}$ values are desirable.

TABLE 3

| | | | | Amine | | | MIC (mg/L) | | | | |
| --- | --- | --- | --- | --- | --- | --- | --- | --- | --- | --- | --- |
| Example | Polymer Name | Carbonyl Monomer | Amine Monomer | Monomer (mol %) | ED-2003 (mol %) | RX | S. Aureus | E. Coli | P. Aeruginosa | C. Albicans | $HC_{50}$ (mg/L) |
| 1 | P31a | DMM | MDEA | 100 | 0 | MeI | >1000 | >1000 | >1000 | 125 | >1000 |
| 2 | P31b | DMM | MDEA | 100 | 0 | DMS | | Not Determined | | | |
| 3 | P31c | DMM | MDEA | 100 | 0 | BnBr | 500 (1000) | 1000 | >1000 | 500 | >1000 |
| 4 | P31d | DMM | MDEA | 100 | 0 | HexBr | 500 (1000) | 1000 | >1000 | 500 | >1000 |
| 5 | P32a | DMM | DAMDPA | 100 | 0 | MeI | >1000 | 63 | 16 | 125 | >1000 |
| 6 | P32b | DMM | DAMDPA | 100 | 0 | DMS | >1000 | 125 | 31 | 500 | >1000 |
| 7 | P32c | DMM | DAMDPA | 100 | 0 | BnBr | 16 | 8 | 63 | 125 | >1000 |
| 8 | P32d | DMM | DAMDPA | 100 | 0 | HexBr | 8 | 8 | 31 | 125 | 875 |
| 9 | P34a | DMM | BAPPIP | 100 | 0 | MeI | ≤4 | 16 | 16 | 500 | >1000 |
| 10 | P34b | DMM | BAPPIP | 100 | 0 | DMS | 16 | 63 | 125 | 250 | >1000 |
| 11 | P34c | DMM | BAPPIP | 100 | 0 | BnBr | | Insoluble | | | |

TABLE 3-continued

| | | | Amine | | | MIC (mg/L) | | | | |
|---|---|---|---|---|---|---|---|---|---|---|
| Example | Polymer Name | Carbonyl Monomer | Amine Monomer | Monomer (mol %) | ED-2003 (mol %) | RX | S. Aureus | E. Coli | P. Aeruginosa | C. Albicans | HC$_{50}$ (mg/L) |
| 12 | P38 | DPC | MDEA | 100 | 0 | MeI | | | Insoluble | | |
| 13 | P48a | DESucc | DAMDPA | 100 | 0 | BnBr | 31 | 8 | 16 | 250 | >1000 |
| 14 | P48b | DESucc | DAMDPA | 95 | 5 | BnBr | 63 | 8 | 63 | 250 | >1000 |
| 15 | P49a | DESucc | DAMDPA | 97.5 | 2.5 | BnBr | 31 | 8 | 16 | 250 | >1000 |
| 16 | P49b | DESucc | DAMDPA | 90 | 10 | BnBr | 63 | 8 | 31 | 250 | >1000 |
| 17 | P59a | DESucc | BAPPIP | 100 | 0 | BnBr | 31 | 16 | 31 | 125 | >1250 |
| 18 | P59b | DESucc | BAPPIP | 100 | 0 | MeI | 8 | 63 | 8 | 63 | >1250 |
| 19 | P59c | DESucc | BAPPIP | 97.5 | 2.5 | BnBr | 16 | 8 | 31 | 125 | >1250 |
| 20 | P59d | DESucc | BAPPIP | 97.5 | 2.5 | MeI | 8 | 31 | 8 | 250 | >1250 |
| 21 | P59e | DESucc | BAPPIP | 95 | 5.0 | BnBr | 16 | 8 | 31 | 250 | >1250 |
| 22 | P59f | DESucc | BAPPIP | 95 | 5.0 | MeI | 16 | 31 | 31 | 125 | >1000 |
| 23 | P60a | DEC | BAPPIP | 97.5 | 2.5 | MeI | 8 | 16 | 250 | 250 | >1000 |
| 24 | P60b* | DEC | BAPPIP | 97.5 | 2.5 | BnBr | 63 | 125 | 250 | 250 | 375 |
| 25 | P73a | DBocG | DAMDPA | 100 | 0 | BnBr | 16 | 63 | 63 | 250 | >1250 |
| 26 | P73b | DBocG | DAMDPA | 97.5 | 2.5 | BnBr | 63 | 32 | 250 | 500 | >1250 |
| 27 | P73c | DBocG | DAMDPA | 95 | 5 | BnBr | 125 | 63 | 250 | 500 | >1250 |
| 28 | P73d | DBocG | DAMDPA | 90 | 10 | BnBr | 63 | 63 | 500 | 500 | >1250 |

*P60b was dissolved in DMSO (final DMSO concentration in the test vial: 1% V/V).

Figure 5:
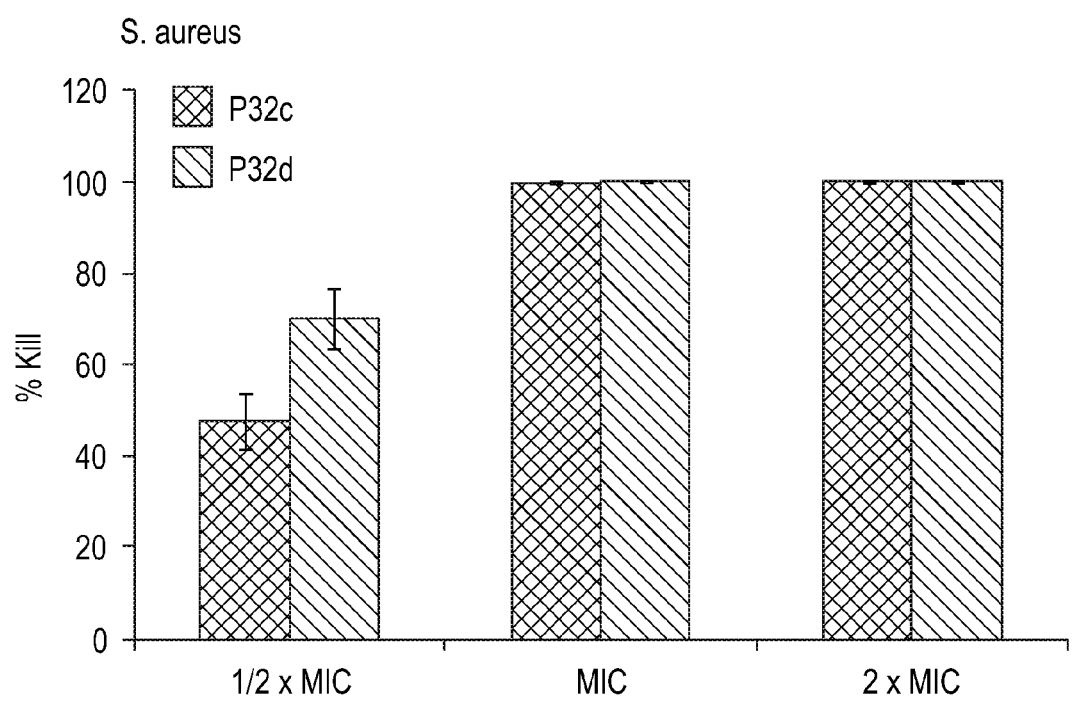
FIG. 5 is a bar graph showing the killing efficiency of cationic polymers P32c and P32d against Staphylococcus aureus (S. aureus) at polymer concentrations of 0.5MIC, 1.0MIC and 2.0MIC.
Figure 6:
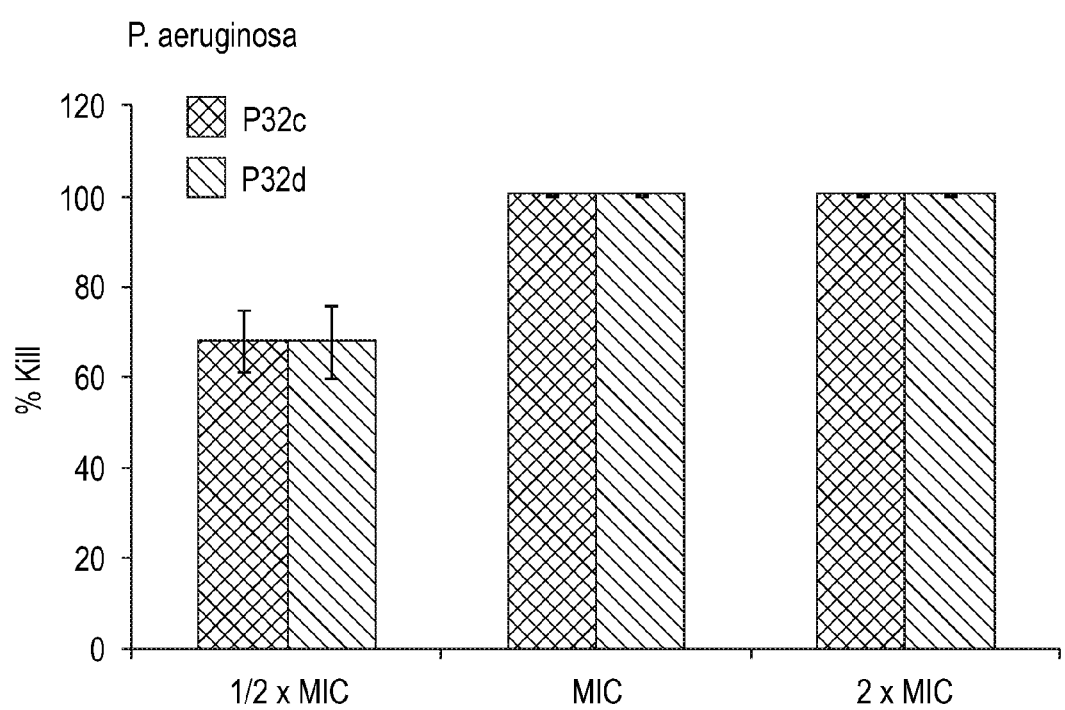
FIG. 6 is a bar graph showing the killing efficiency of cationic polymers P32c and P32d against Pseudomonas aeruginosa (P. aeruginosa) at polymer concentrations of 0.5MIC, 1.0MIC and 2.0MIC.
Figure 7:
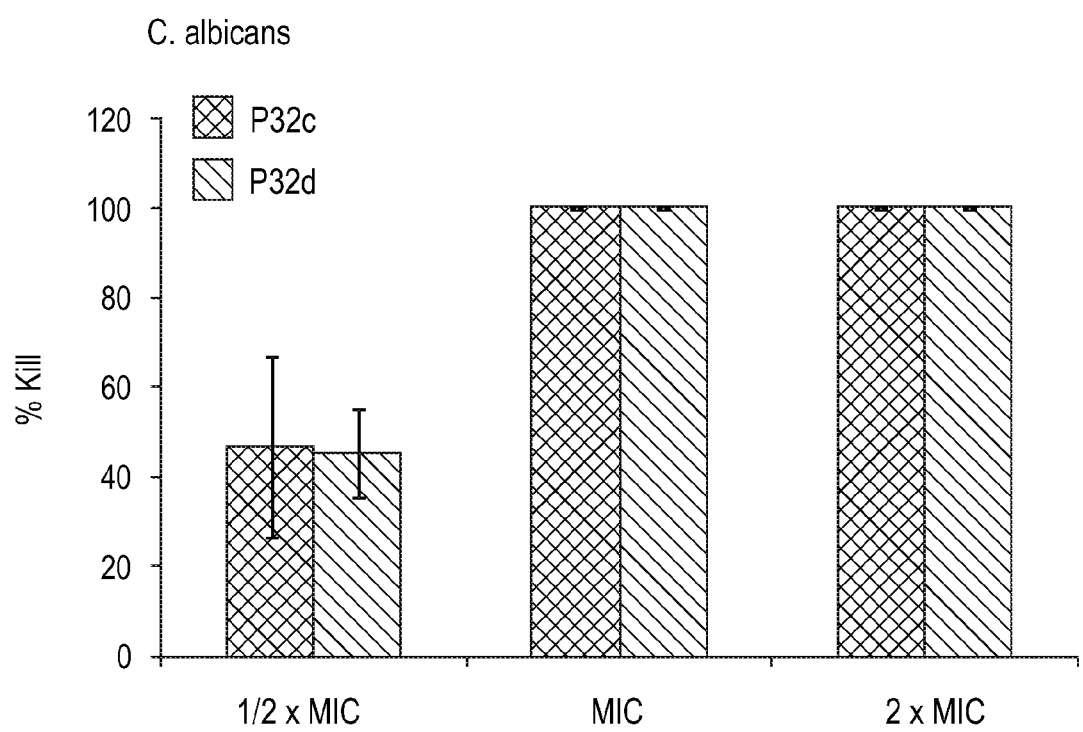
FIG. 7 is a bar graph showing the killing efficiency of cationic polymers P32c and P32d against Candida albicans (C. albicans) at polymer concentrations of 0.5MIC, 1.0MIC and 2.0MIC.
Figure 8:
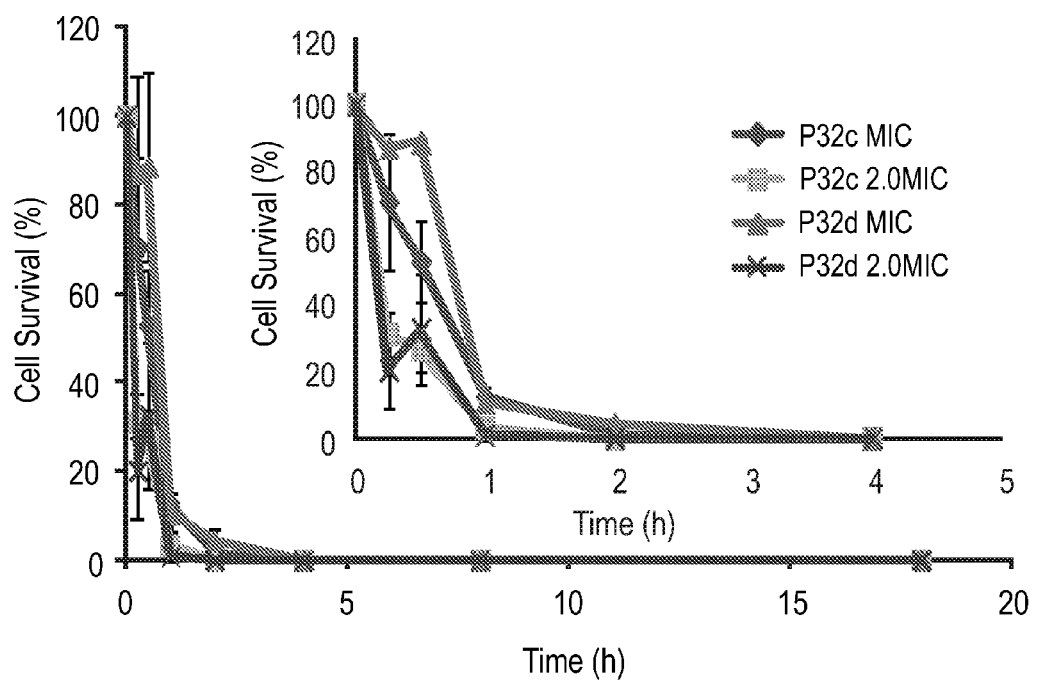
FIG. 8 is a pair of graphs showing the killing kinetics of cationic polymers P32c and P32d at respective concentrations of 1.0MIC and 2.0MIC against S. aureus.

Among the polymers of the 31, 32, 34 and 38 series, the MIC values for P32c and P32d were the lowest of all microbes tested, without inducing significant hemolytic effect or toxicity towards the red blood cells. The respective killing efficiency of both polymers on Gram-positive S. aureus, Gram-negative P. aeruginosa and fungi C. albicans was then further evaluated. Using polymers P32c and P32d, each at a concentration of MIC or 2.0MIC (2×MIC), at least 99.9% of bacteria were eradicated after 18 hours of incubation, and at least 99.9% of fungi were eradicated after 42 hours, as illustrated in the bar graphs of FIG. 5 (S. aureus), FIG. 6 (P. aeruginosa), and FIG. 7 (C. albicans). This result was also obtained in the case of multidrug-resistant P. aeruginosa, indicating the effectiveness of the polymers. The duration needed for the polymers to achieve 99.9% killing efficiency was also assessed using S. aureus as the model microbes. As shown in FIG. 8 (overlapping pair of graphs), more than 50% of the bacteria were killed after 30 minutes exposure to 2.0MIC concentration of polymers P32c and P32d. A killing efficiency of 99.9% was achieved within 4 hours and 2 hours of treatment at MIC concentration and 2.0MIC, respectively. Based on this trend, the duration is expected to further decrease at increased concentration of each polymer.

Figure 9:
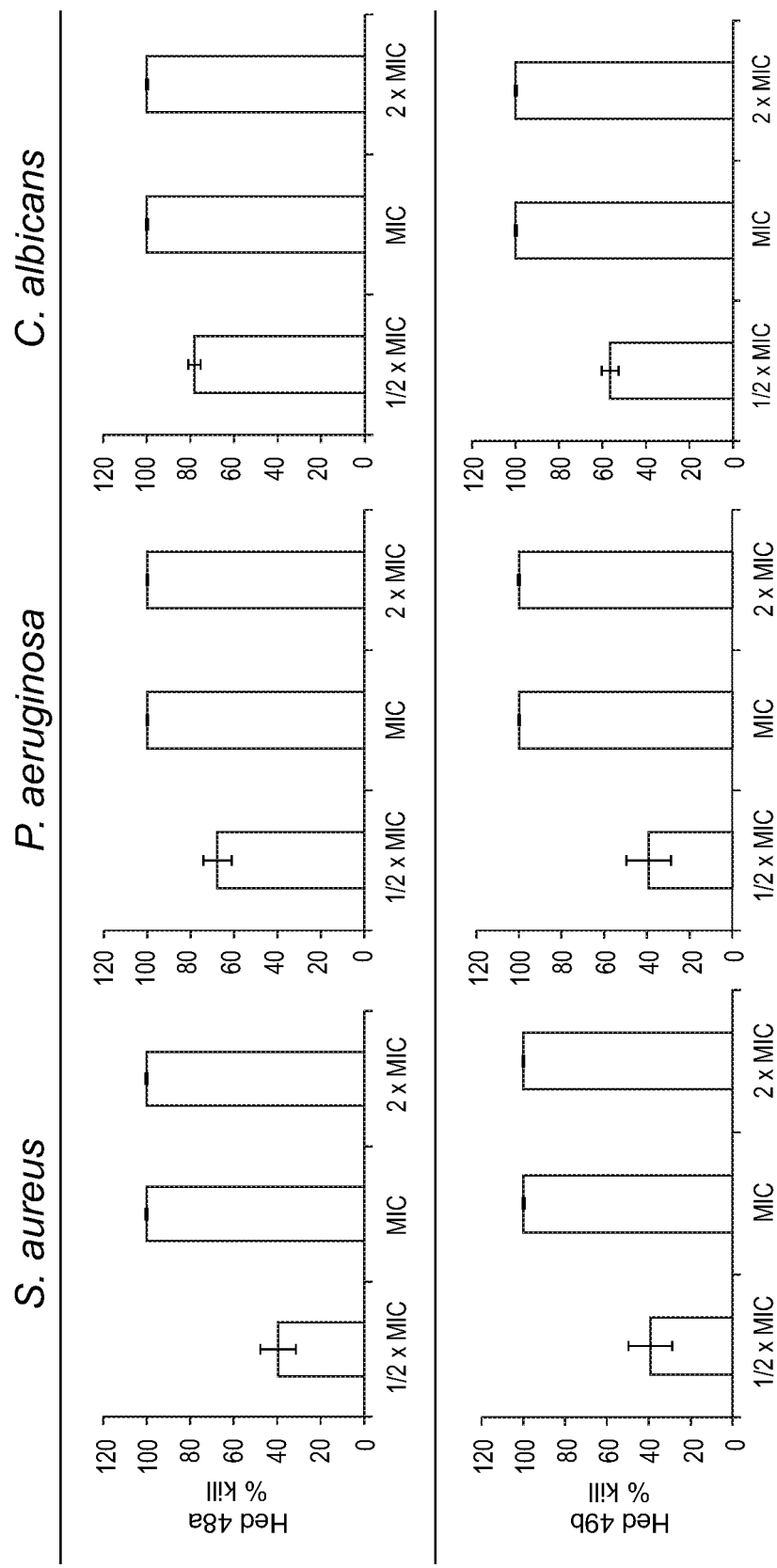
FIG. 9 is a series of bar charts comparing the killing efficiency of cationic polymers P48a and P49b at concentrations of 0.5MIC, 1.0MIC and 2.0MIC against S. aureus, P. aeruginosa, and C. albicans.

The respective MIC values of polymers P48a, P48b, P49a and P49b against S. Aureus, E. Coli and P. Aeruginosa were similar to those of P32c and P32d. The presence of JEFFAMINE, even at 10 mol %, did not appear to reduce the antibacterial activity of polymers. P48a without JEFFAMINE and P49b with 10 mol % JEFFAMINE were selected to test for killing efficiency against S. aureus, P. Aeruginosa and C. albicans. The results are shown in FIG. 9 (series of bar graphs). The polyether chain of JEFFAMINE did not weaken the effectiveness of polymer against bacteria/fungi. At least 99.9% of bacteria and fungi were eliminated after 18 hours incubation at MIC and 2.0MIC concentrations.

Cell Viability

Figure 10:
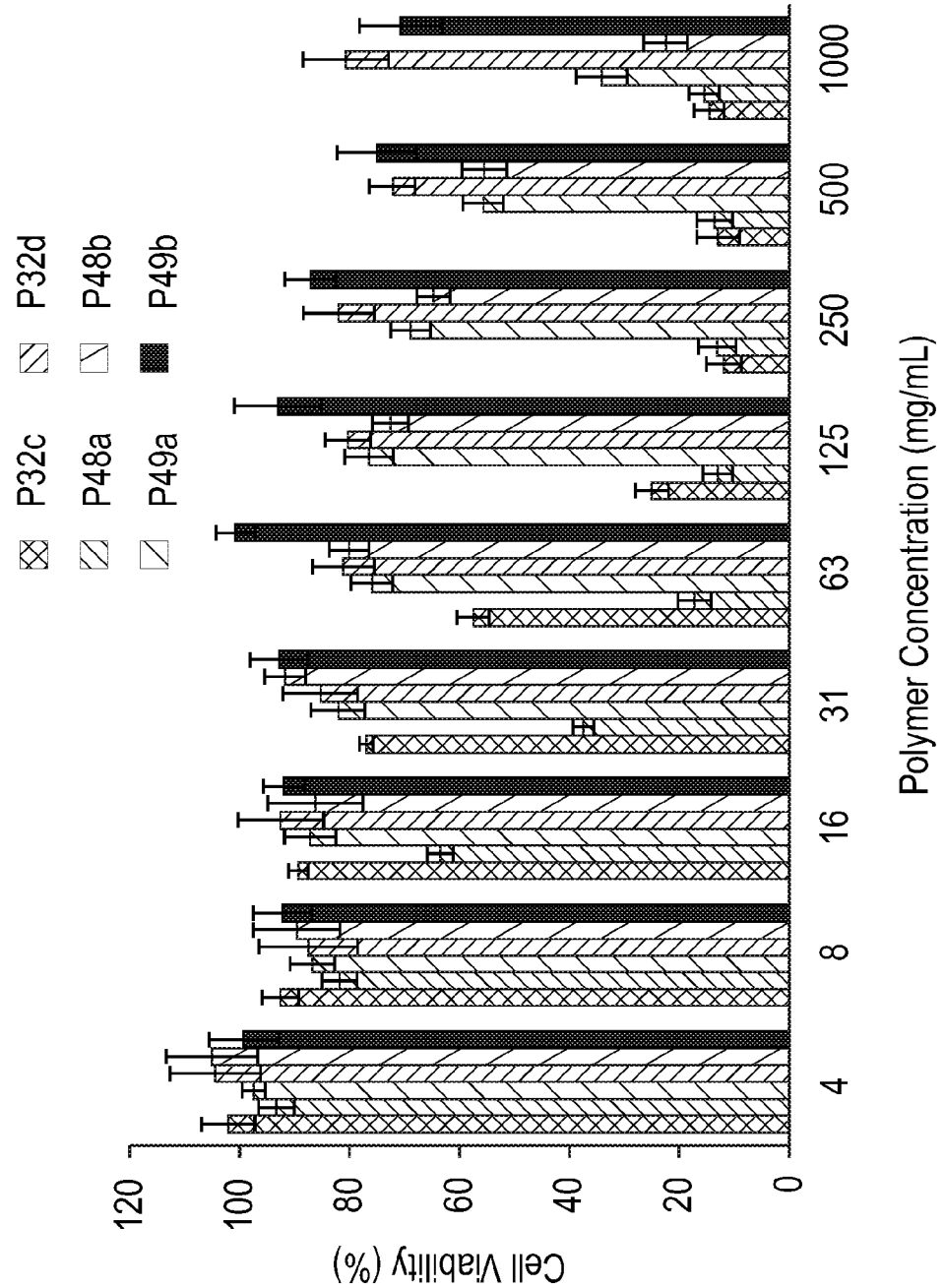
FIG. 10 is a bar chart showing human dermal fibroblast (HDF) cell viability after a 6 hour treatment with various concentrations of cationic polymers P32c, P32d, P48a, P48b, P49a and P49b.

Through MTT assay, cytotoxicity of polymers P32c, P32d, P48a, P48b, P49a, and P49b was evaluated using the HDF cell line. The resulting cell viability is depicted in FIG. 10 (bar graph). Whereas P32c and P32d were effective against the microbes, they have shown to be toxic to the cells. Less than 80% cells remained viable after 6 hours of treatment with P32c at 31 mg/L, and with P32d at 16 mg/L.

On the contrary, cell viability was clearly higher at these concentrations when the HDF cells were treated with the P48 and P49 polymers prepared with JEFFAMINE. In particular, even at 1000 mg/L, more than 60% cells survived after treatment with P48b and P49b, indicating that the presence of JEFFAMINE significantly reduced the cytotoxicity of polymers, even at the high concentrations. This result demonstrates that the biodegradable polyamides are promising antimicrobial agents for use in consumer care products.

The polyamides of the 59 polymer series were similarly effective against the bacteria tested as compared to the polyamides of 48 and 49 series (P48a versus P59a, P49a versus P59c, P48b versus P59e). Polyamide P59d and polyurea P60a had low MIC values against E. coli, indicating that the urea groups in the backbone of the polymer might not adversely affect antimicrobial activity.

CONCLUSION

Antimicrobial polymers that were synthesized by condensation polymerization and quaternized show excellent water-solubility and potent antimicrobial activity against a panel of clinically relevant microbes including multi-drug resistant P. aeruginosa. The polymers contain amide bonds that remain intact in aqueous solution, including weakly alkaline environments, making them attractive for personal care products due to their longer shelf-life. On the other hand, the amide bond is enzymatically degradable, which avoids eco-toxicity. The use of succinate monomer improved cell viability at comparable antimicrobial potency relative to the 2-methylmalonate monomer (compare P48a with P32c in FIG. 10 at 250 mg/L concentration). Further improvement in cell viability at comparable antimicrobial potency was obtained by the introduction of JEFFAMINE in an amount up to 10 mol % (compare P48a with P48b in FIG. 10 at 1000 mg/L concentration).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A cationic polymer, comprising:
   i) a cationic repeat unit of formula (1):

$$*-\left(W'-\overset{O}{\underset{1}{C}}-\overset{H}{N}-L^a-Q'-L^b-\overset{H}{\underset{2}{N}}\right)-*, \quad (1)$$

wherein
   W' is a single bond or a divalent linking group having a structure *—C(=O)-L'-*, wherein L' is divalent radical comprising 1-20 carbons and L' is linked to carbon 1, nitrogen labeled 2 is designated a tail and W' is designated a head,
   $L^a$ and $L^b$ are independent divalent hydrocarbon groups comprising 2-20 carbons, and
   Q' is a divalent radical selected from group consisting of $$*-\overset{R^a}{\underset{R^b}{\overset{|+}{N}}}-*, \quad X^- \quad (4)$$

$$*-\overset{R^c}{\underset{X^-}{\overset{+}{N}}}\diagdown N-*, \quad (5)$$

$$*-\overset{R^c}{\underset{X^-}{\overset{+}{N}}}\diagdown \overset{R^d}{\underset{X^-}{\overset{+}{N}}}-*, \text{ and} \quad (6)$$

$$\text{(pyridinium with } R^e, X^-) \quad (7)$$

wherein $R^a$, $R^b$, $R^c$, $R^d$, $R^e$ are independent monovalent hydrocarbon groups comprising 1-20 carbons and each $X^-$ is an independent negative-charged counterion; and ii) a polymeric repeat unit of formula (8):

$$*-\left(W''-\overset{O}{\underset{1}{C}}-\overset{H}{N}-L^c-P'-L^d-\overset{H}{\underset{2}{N}}\right)-*, \quad (8)$$

wherein
   nitrogen labeled 2 is designated a tail,
   W'' is designated a head,
   W'' is a single bond or a divalent linking group having a structure *—C(=O)-L''-*, wherein L'' is divalent radical comprising 1-20 carbons and L'' is linked to carbonyl carbon 1,
   $L^c$ and $L^d$ are independent divalent linking groups selected from the group consisting of a single bond, and hydrocarbon groups comprising 1-6 carbons, and
   P' is a divalent poly(alkylene oxide) chain;
wherein
   the cationic repeat unit and the polymeric repeat unit are covalently linked in a head-to-tail arrangement.

2. The cationic polymer of claim 1, wherein the cationic polymer is a random copolymer.

3. The cationic polymer of claim 1, wherein L' is selected from the group consisting of methylene, 1,2-ethylene, 1,1-ethylene, 1,3-propylene, 1,1-propylene, 1,4-butylene, 1,1-butylene, 1,5-pentylene, and 1,1-pentylene.

4. The cationic polymer of claim 1, wherein L'' is selected from the group consisting of methylene, 1,2-ethylene, 1,1-ethylene, 1,3-propylene, 1,1-propylene, 1,4-butylene, 1,1-butylene, 1,5-pentylene, and 1,1-pentylene.

5. The cationic polymer of claim 1, wherein W' is a single bond.

6. The cationic polymer of claim 1, wherein W' is a *—C(=O)-L'-*.

7. The cationic polymer of claim 1, wherein W'' is a single bond.

8. The cationic polymer of claim 1, wherein W'' is a *—C(=O)-L''-*.

9. The cationic polymer of claim 1, wherein P' is a block copolymer chain comprising a poly(propylene oxide) block and a poly(ethylene oxide) block.

10. The cationic polymer of claim 1, wherein the cationic polymer comprises the polymeric repeating units in an amount of more than 0 mol % to about 10 mol % based on total moles of repeating units of the cationic polymer.

11. The cationic polymer of claim 1, wherein the cationic polymer comprises the polymeric repeating units in an amount of about 2.5 mol % to about 10 mol % based on total moles of repeating units of the cationic polymer.

12. The cationic polymer of claim 1, wherein P' is a triblock copolymer having a structure according to formula (9):

$$\dashv\left[O\diagdown\diagup\right]_r\left[O\diagdown\diagup\right]_s\left[O\diagdown\diagup\right]_t * , \quad (9)$$

wherein
   r, s, and t represent degrees of polymerization of respective blocks of alkylene oxide repeat units enclosed in the brackets, and r, s, and t independently have average values greater than 1.

13. The cationic polymer of claim 1, wherein P' has a number average molecular weight (Mn) of about 500 to about 5000.

14. The cationic polymer of claim 1, wherein P' has a number average molecular weight (Mn) of about 1500 to about 2500.

15. The cationic polymer of claim 1, wherein the polymeric repeat unit has a structure in accordance with formula (10):

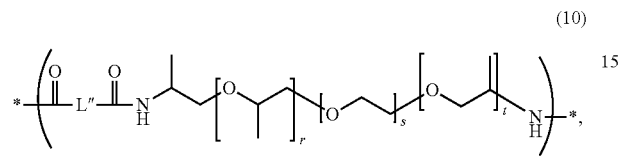

wherein
L" is a divalent group comprising 1-20 carbons,
r, s, and t represent average numbers of respective alkylene oxide repeat units, and
r, s, and t independently have average values greater than 1.

16. The cationic polymer of claim 10, wherein s/(r+t) has a value of about 2 to about 12.

17. The cationic polymer of claim 1, wherein $R^a$ is methyl and $R^b$ is benzyl.

18. The cationic polymer of claim 1, wherein $R^c$, $R^d$, and $R^e$ are independently selected from the group consisting of methyl and benzyl.

19. The cationic polymer of claim 1, wherein L' is methylene.

20. The cationic polymer of claim 1, wherein L' is

(1,1-ethylene).

21. The cationic polymer of claim 1, wherein L' is

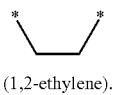

(1,2-ethylene).

22. The cationic polymer of claim 1, wherein L" is methylene.

23. The cationic polymer of claim 1, wherein L" is

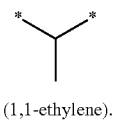

(1,1-ethylene).

24. The cationic polymer of claim 1, wherein L" is

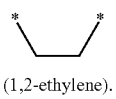

(1,2-ethylene).

25. A method of killing a microbe, comprising contacting the microbe with the cationic polymer of claim 1.

26. The method of claim 25, where the microbe is selected from the group consisting of Gram-positive microbes, Gram-negative microbes, fungi, and combinations thereof.

27. An antimicrobial composition comprising the cationic polymer of claim 1 and at least one other chemical component.

28. The antimicrobial composition of claim 27, wherein the antimicrobial composition is selected from the group consisting of soaps, shampoos, skin lotions, skin creams, cosmetics, mouthwashes, wound care agents, deodorants, surface cleaning agents, and laundry detergents.

29. The antimicrobial composition of claim 27, wherein the antimicrobial composition is toxic to a microbe selected from the group consisting of Gram-positive microbes, Gram-negative microbes, fungi, and combinations thereof.

* * * * *